United States Patent
Osterfeld et al.

(10) Patent No.: US 10,267,871 B2
(45) Date of Patent: Apr. 23, 2019

(54) MAGNETIC TUNNEL JUNCTION SENSORS AND METHODS FOR USING THE SAME

(71) Applicant: MagArray, Inc., Sunnyvale, CA (US)

(72) Inventors: Sebastian J. Osterfeld, Mountain View, CA (US); Shan Xiang Wang, Palo Alto, CA (US)

(73) Assignee: MagArray, Inc., Milpitas, CA (US)

(*) Notice: Subject to any disclaimer, the term of this patent is extended or adjusted under 35 U.S.C. 154(b) by 0 days.

(21) Appl. No.: 14/209,863

(22) Filed: Mar. 13, 2014

(65) Prior Publication Data

US 2014/0266186 A1    Sep. 18, 2014

Related U.S. Application Data

(60) Provisional application No. 61/792,257, filed on Mar. 15, 2013.

(51) Int. Cl.
*G01R 33/09*    (2006.01)
*G01N 27/74*    (2006.01)

(52) U.S. Cl.
CPC .......... *G01R 33/098* (2013.01); *G01N 27/745* (2013.01)

(58) Field of Classification Search
CPC ........ G01R 3/00; G01R 33/12; G01R 33/098; G01R 33/09; G01R 33/091; G01R 33/1269; G01N 27/72; G01N 27/745; G01N 33/54326; G01N 35/0098; C12Q 2563/143; C12Q 2563/6837; B82Y 5/00

(Continued)

(56) References Cited

U.S. PATENT DOCUMENTS 5,981,297 A    11/1999 Baselt
6,057,176 A    5/2000 King
(Continued)

FOREIGN PATENT DOCUMENTS

JP    2001094173    4/2001
JP    2004165441    6/2004
(Continued)

OTHER PUBLICATIONS

Baselt et al., "A Biosensor Based on Magnetoresistance Technology", Biosensors & Bioelectronics, Oct. 1998, 13(7-8):731-739.
(Continued)

*Primary Examiner* — Jeff W Natalini
*Assistant Examiner* — Steven L Yeninas
(74) *Attorney, Agent, or Firm* — Rudy J. Ng; Bret E. Field; Bozicevic, Field & Francis LLP

(57) ABSTRACT

Provided are magnetic sensors, which include a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping. Also provided are devices, systems and methods in which the subject magnetic sensors find use.

25 Claims, 11 Drawing Sheets

(58) Field of Classification Search
USPC .......... 324/252, 228, 244, 207.25, 247, 249; 438/48; 365/185; 436/149, 164, 174; 257/421
See application file for complete search history.

(56) References Cited

U.S. PATENT DOCUMENTS

| | | | |
|---|---|---|---|
| 6,323,634 B1 | 11/2001 | Nakagawa et al. | |
| 6,582,921 B2 | 6/2003 | Mirkin et al. | |
| 6,623,983 B1 | 9/2003 | Terstappen et al. | |
| 6,679,130 B2 | 1/2004 | Hajduk et al. | |
| 6,736,978 B1 * | 5/2004 | Porter ................. | G01F 1/708 210/222 |
| 6,743,639 B1 | 6/2004 | Tondra et al. | |
| 6,819,532 B2 | 11/2004 | Kamijo | |
| 7,504,262 B2 | 3/2009 | Fox | |
| 7,906,345 B2 | 3/2011 | Wang et al. | |
| 7,977,111 B2 | 7/2011 | Shi et al. | |
| 2002/0014408 A1 | 2/2002 | Schroeder | |
| 2002/0060565 A1 | 5/2002 | Tondra | |
| 2003/0204133 A1 | 10/2003 | Harjunmaa et al. | |
| 2004/0002121 A1 | 1/2004 | Regan et al. | |
| 2004/0002169 A1 | 1/2004 | Kraus, Jr. et al. | |
| 2005/0025969 A1 | 2/2005 | Berning et al. | |
| 2005/0100930 A1 * | 5/2005 | Wang ................. | B82Y 5/00 435/6.12 |
| 2007/0003994 A1 | 1/2007 | Simpson et al. | |
| 2007/0122898 A1 | 5/2007 | Sharma | |
| 2007/0178504 A1 | 8/2007 | Colpitts et al. | |
| 2007/0297101 A1 | 12/2007 | Inomata et al. | |
| 2008/0024117 A1 | 1/2008 | Hong et al. | |
| 2008/0160622 A1 | 7/2008 | Su et al. | |
| 2008/0258721 A1 * | 10/2008 | Guo et al. .............. | 324/252 |
| 2009/0104707 A1 | 4/2009 | Wang et al. | |
| 2010/0213934 A1 * | 8/2010 | Wang et al. ........... | 324/252 |
| 2010/0248973 A1 * | 9/2010 | Van Lankvelt ....... | G01N 27/745 506/7 |
| 2011/0027901 A1 | 2/2011 | Gaster et al. | |
| 2012/0134200 A1 | 5/2012 | Khoueir et al. | |
| 2012/0193736 A1 * | 8/2012 | Mather ................. | G01R 33/098 257/421 |
| 2012/0231960 A1 | 9/2012 | Osterfeld et al. | |
| 2012/0281461 A1 * | 11/2012 | Asao ................. | G11C 11/16 365/158 |
| 2013/0241536 A1 * | 9/2013 | Cambou .............. | G01R 33/096 324/207.14 |

FOREIGN PATENT DOCUMENTS

| | | |
|---|---|---|
| JP | 2004/205495 | 7/2004 |
| WO | WO 01/14591 | 3/2001 |
| WO | WO 01/57506 | 8/2001 |
| WO | WO 03/031977 | 4/2003 |
| WO | WO 03/054523 | 7/2003 |
| WO | WO 03/081202 | 10/2003 |
| WO | WO 2007/014322 | 2/2007 |
| WO | 2007040991 | 4/2007 |
| WO | WO 2008/001261 | 1/2008 |
| WO | WO 2008/107691 | 9/2008 |
| WO | WO 2009/013668 | 1/2009 |
| WO | WO 2010/074369 | 7/2010 |
| WO | 20130134410 | 9/2013 |

OTHER PUBLICATIONS

Bozorth, "Ferromagnetism", D. Van Nostrand Company, Inc. (1951), pp. 190-209.
Ferreira et al., "Biodetection using magnetically labeled biomolecules and arrays of spin valve sensors (invited)", Journal of Applied Physics, May 15, 2003, 93(10):7281-7286, XP012058127, ISSN:0021-8979.
Ferreira et al., "Detection of biomolecular recognition using nanometer-sized magnetic labels and spin-valve sensors", Digest of Intermag 2003, IEEE International Magnetics Conference, Mar. 28, 2003, pp. EC-4, XP010665265, ISBN:0-7803-7647-1.
Freitas et al., "Magnetoresistive biochips", Europhysics News, Nov. 2003, 34(6):224-226, XP002429397, ISSN:0531-7479.
Graham et al., "High sensitivity detection of molecular recognition using magnetically labelled biomolecules and magnetoresistive sensors", Biosensors & Bioelectronics, Apr. 1, 2003, 18(4):483-488, XP002429396.
Graham et al.; "Single Magnetic Microsphere Placement and Detection on-chip Using Current Line Designs with Integrated Spin Valve Sensors: Biotechnological Applications", J. Appl. Phys. (2002), 91(10):7786-88.
Han et al., "A High-Density Magnetoresistive Biosensor Array with Drift-Compensation Mechanism", 2007 IEEE International Solid-State Circuits Conference (2007), Session 8, pp. 168-169, 594.
Han et al., "CMOS Integrated DNA Microarray Based on GMR Sensors", Electron Devices Meeting (2006), pp. 1-4.
Lagae et al., "On-chip manipulation and magnetization assessment of magnetic bead ensembles by integrated spin-valve sensors", Journal of Applied Physics, May 15, 2002, 91(10):7445-7447, XP012054843, ISSN:0021-8979.
Li et al., "Analytical and Micromagnetic Modeling for Detection of a Single Magnetic Microbead or Nanobead by Spin Valve Sensors", IEEE Trans. Magn. (2003), 39(5):3313-3315.
Li et al., "Detection of Single Micron-Sized Magnetic Bead and Magnetic Nanoparticles Using Spin Valve Sensors for Biological Applications", J. Appl. Phys. (2003), 93(10):7557-7559.
Li et al., "Spin Valve Sensors for Ultrasensitive Detection of Superparamagnetic Nanoparticles for Biological Applications", Sens Actuators A Phys (2006), 126(1):98-106.
Miller et al., "A DNA Array Sensor Utilizing Magnetic Microbeads and Magnetoelectronic Detection", Journal of Magnetism and Magnetic Materials (2001), 225:138-144.
Murray et al., "Monodisperse 3d Transition-Metal (Co, Ni, Fe) Nanoparticles and Their Assembly into Nanoparticle Superlattices", MRS Bulletin (2001), vol. 26 (12): pp. 985-991.
Parkin et al., "Exchange-Biased Magnetic Tunnel Junctions and Application to Nonvolatile Magnetic Random Access Memory (Invited)", J. Appl. Phys. (1999), 85(8):5828-5833.
Parkin et al., "Oscillations in Exchange Coupling and Magnetoresistance in Metallic Superlattice Structures: Co/Ru, Co/Cr, and Fe/Cr", Phys. Rev. Lett. (1990), 64(19):2304-7.
Schena et al., "Technology Standards for Micoarray Research", Microarray Biochip Technology Chapter 1, Eaton Publishing, (2000), pp. 1-18.
Sellmyer et al., "Magnetism of Nanophase Composite Films", Handbook of Thin Film Materials Chapter 7, Edited by: Nalwa, H.S., Stanford Scientific Corporation; Academic Press (2002), 5:337-374.
Slonczewski et al., "Micromagnetics of Laminated Permalloy Films" IEEE Trans. Magn. (1998), 24(3):2045-2054.
Sun et al., "Monodisperse $MFe_2O_4$ (M=Fe, Co, Mn) Nanoparticles", IBM T. J. Watson Research Center, Yorktown Heights, NY; pp. 1-24.
Sun et al., "Polymer Mediated Self-Assembly of Magnetic Nanoparticles" J. Am. Chem. Soc. (2002), 124(12):2884-2885.
Sun et al., "Synthesis of Monodisperse Cobalt Nanocrystals and their Assembly into Magnetic Superlattices (invited)", J. Appl. Phys. (1999), 85(8):4325-30.
Tehrani et al., "Recent Developments in Magnetic Tunnel Junction MRAM" IEEE Trans. Magn. (2000), 36(5):2752-2757.
Thorsen et al., "Microfluidic Large-Scale Integration" Science (2002), 298:580-584.
Trademark Electronic Search System (Tess) for "MAGARRAY" http://tess2.uspto.~ov/bin/showfield?f=doc&state=ut16qp.2.10;9 11 Mar. 2004, 3 pages.
Van De Veerdonk et al., "Current Distribution Effects in Magnetoresistive Tunnel Junctions;" Appl. Phys. Lett. (1997), 71(19):2839-2841.

(56) References Cited

OTHER PUBLICATIONS

Wang et al., "Design and Fabrication of Bio-Magnetic Sensors and Magnetic Nanobead Labels for DNA Detection and Identification", Digest of Intermag 2003, IEEE International Magnetics Conference, Mar. 28, 2003, pp. EC-1, XP01066526, ISBN: 0-7803-7647-1.
Xu et al., "Giant Magnetoresistive Biochip for DNA Detection and HPV Genotyping", Biosens Bioelectron (2008), 24(1):99-103.

\* cited by examiner

MAGNETIC TUNNEL JUNCTION SENSORS AND METHODS FOR USING THE SAME

CROSS-REFERENCE TO RELATED APPLICATION

Pursuant to 35 U.S.C. § 119(e), this application claims priority to the filing date of U.S. Provisional Application Ser. No. 61/792,257 filed on Mar. 15, 2013, the disclosure of which is incorporated herein by reference.

STATEMENT REGARDING FEDERALLY SPONSORED RESEARCH

This invention was made with government support under Contract Number HHSN216200900011C, awarded by the National Institutes of Health. The government has certain rights in the invention.

INTRODUCTION

Biomarkers (also called disease signatures) are specific analytes like RNA, DNA and proteins that can be used as surrogates for a mechanism of action, disease state or clinical endpoint. In particular, multiplexed or multimarker approaches may be used in molecular diagnostics and personalized medicine, whose goal is to identify the right treatment for the right patient at the right time and dose, or to detect early complex diseases such as cancer and cardiovascular diseases sensitively and specifically. DNA and protein microarrays have been developed to accommodate a large number of biomarkers.

Most commercial DNA microarray systems utilize fluorescent labeling (tagging) to quantify biomolecular analytes (targets). They may be of limited sensitivity because they require approximately $10^4$ or more molecules to achieve a useful signal-to-noise ratio and are marginally quantitative because of the optical systems involved, and also because of crosstalk and bleaching. The optical detection systems are usually used in conjunction with amplification techniques such as polymerase chain reaction (PCR) which multiplies the original biomolecules by many orders of magnitude. Alternative microarray technologies with a higher sensitivity, lower cost, and better portability are sought after. Such technologies can open many new applications in the field of molecular diagnostics and genomics.

SUMMARY

Provided are magnetic sensors, which include a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping. Also provided are devices, systems and methods in which the subject magnetic sensors find use.

Aspects of the present disclosure include a magnetic sensor. The magnetic sensor includes a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping.

In some embodiments, the first electrode contacts substantially the entire surface of the MTJ magnetoresistive element.

In some embodiments, the second electrode contacts substantially the entire opposing surface of the MTJ magnetoresistive element.

In some embodiments, an edge of the second electrode is aligned with the edge of the opposing surface of the MTJ magnetoresistive element.

In some embodiments, the magnetic sensor includes a passivation layer disposed on the first electrode.

In some embodiments, the magnetic sensor includes an analyte-specific probe bound to a surface of the magnetic sensor.

Aspects of the present disclosure include a magnetic sensor device. The magnetic sensor device includes a magnetic sensor array having two or more magnetic sensors. Each magnetic sensor includes a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping.

In some embodiments, the magnetic sensors are electrically connected in series by the first and second electrodes.

In some embodiments, one or more magnetic sensors include an analyte-specific probe bound to a surface of the magnetic sensor.

In some embodiments, the magnetic sensor array includes two or more distinct magnetic sensors each configured to specifically detect the same analyte.

In some embodiments, the magnetic sensor array includes two or more distinct magnetic sensors each configured to specifically detect a different analyte.

Aspects of the present disclosure include a magnetic sensor system. The magnetic sensor system includes a magnetic sensor device that includes a magnetic sensor array having two or more magnetic sensors. Each magnetic sensor includes a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping. The magnetic sensor system further includes a magnetic field source.

In some embodiments, the magnetic sensor system includes a processor configured to obtain an analyte-specific signal from the magnetic sensor device.

Aspects of the present disclosure include a method for evaluating whether an analyte is present in a sample. The method includes contacting a magnetic sensor with a sample to generate a signal, obtaining a signal from the magnetic sensor, and evaluating whether the analyte is present in each sample based on the signal. The magnetic sensor includes a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping.

In some embodiments, the magnetic sensor includes an analyte-specific probe bound to a surface of the magnetic sensor.

In some embodiments, the method includes magnetically labeling the sample prior to the contacting.

In some embodiments, the evaluating includes obtaining a signal from the magnetic sensor as the magnetically-labeled sample contacts the magnetic sensor. In some embodiments, the signal is an analyte-specific signal.

In some embodiments, the contacting includes applying a magnetic label to the magnetic sensor after contacting the magnetic sensor with the sample.

Aspects of the present disclosure include a kit that includes a magnetic sensor device and a magnetic label. The magnetic sensor device includes a magnetic sensor array comprising two or more magnetic sensors. Each magnetic sensor includes a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping.

In some embodiments, the magnetic label is a magnetic nanoparticle.

DETAILED DESCRIPTION

Figure 1:
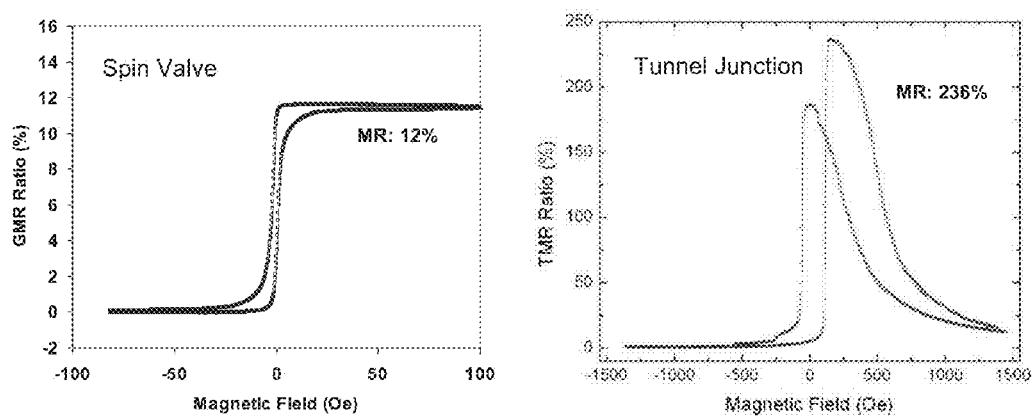
FIG. 1 shows a graph of a Magnetic Response (Transfer Curve) of a GMR Spin Valve sensor, 12% (left) vs. Magneto Tunnel Junction, 236% (right). The magnetoresistances shown here are representative for each type of device. This shows that a MTJ based sensor can be significantly more sensitive than a spin valve based sensor.

Provided are magnetic sensors, which include a magnetic tunnel junction (MTJ) magnetoresistive element, a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping. Also provided are devices, systems and methods in which the subject magnetic sensors find use.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the subject magnetic sensors are described first in greater detail, followed by a description of the magnetic sensor devices, systems and methods in which the subject magnetic sensors find use.

Magnetic Sensors

Aspects of the present disclosure include a magnetic sensor. In some instances, the magnetic sensor is configured to minimize electrical shorting that may occur between electrodes connected to the sensor. For example, the magnetic sensor may include a magnetoresistive element and two electrodes connected to the magnetoresistive element, where the magnetic sensor is configured to minimize the occurrence of electrical shorting between the two electrodes. Minimizing electrical shorting between the two electrodes may facilitate an increase in the accuracy of the sensor.

In certain embodiments, the magnetic sensor includes a magnetic tunnel junction (MTJ) magnetoresistive element (also referred to herein as an MTJ element), a first electrode contacting at least a portion of a surface of the MTJ magnetoresistive element and extending beyond an edge of the surface of the MTJ magnetoresistive element, and a second electrode contacting at least a portion of an opposing surface of the MTJ magnetoresistive element and extending beyond an edge of the opposing surface of the MTJ magnetoresistive element, where facing surfaces of the extending portions of the first and second electrodes are non-overlapping. Additional aspects of MTJ magnetoresistive elements are described in more detail in the sections below.

In certain embodiments, the first electrode contacts at least a portion of the surface of the MTJ magnetoresistive element. By at least a portion is meant that the electrode contacts a sufficient surface area of the electrode to make an electrical contact sufficient for the operation of the sensor to detect an analyte of interest. In some cases, the electrode may contact 10% or more of the surface of the MTJ electrode, such as 20% or more, or 30% or more, or 40% or more, or 50% or more, or 60% or more, or 70% or more, or 80% or more, or 90% or more, or in some embodiments, may contact substantially the entire surface area of one surface of the MTJ element, e.g., the top surface of the MTJ element, or the bottom surface of the MTJ element.

Similarly, the second electrode may contact at least a portion of the opposing surface of the MTJ element. As such, the first and second electrodes contact opposing surfaces the MTJ element. For example, the first electrode may contact at least a portion of the top surface of the MTJ element, and the second electrode may contact at least a portion of the bottom surface of the MTJ element. The opposite arrangements of electrodes is also possible where the first electrode contacts at least a portion of the bottom surface of the MTJ element and the second electrode contacts at least a portion of the top surface of the MTJ element.

In certain embodiments, the first electrode contacts a portion of the surface of the electrode, e.g., less than 100% of the surface area of the contacted surface of the MTJ element. For example, the first electrode may contact a portion of the top surface of the MTJ element. In certain instances, the second electrode contacts substantially the entire opposing surface of the MTJ sensor, e.g., substantially the entire bottom surface of the MTJ element.

In certain embodiments, the first electrode extends beyond an edge of the surface of the MTJ element. By extending beyond the edge is meant that the electrode has a portion (e.g., an end portion) that contacts the surface of the MTJ element as described above, and includes a portion that overhangs the edge of the MTJ element. For example, the electrode may be a planar electrode where an end portion of the planar electrode contacts the surface of the MTJ element, and the remaining portion of the planar electrode sticks out past the edge of the MTJ element. The first electrode may extend beyond an edge of the surface of the MTJ element, such as the top surface of the MTJ element.

Similarly, the second electrode may extend beyond the edge of the opposing surface of the MTJ element. As described above, the second electrode may have a portion (e.g., an end portion) that contacts the opposing surface (e.g., the surface of the MTJ element opposite the surface contacted by the first electrode) of the MTJ element, and a remaining portion of the second electrode may overhang the edge of the MTJ element. For instance, the second electrode may be a planar electrode where an end portion of the second planar electrode contacts the opposing surface of the MTJ element, and the remaining portion of the second planar electrode sticks out past the edge of the MTJ element. The second electrode may extend beyond an edge of the surface of the MTJ element, such as the bottom surface of the MTJ element.

As described above, the first electrode includes an extending portion that overhangs an edge of the MTJ element, and as such the first electrode has outward facing and inward facing surfaces, where the outward facing surface is facing away from the MTJ element and the inward facing surface is facing towards the MTJ element. Similarly, the second electrode includes an extending portion the overhangs an edge of the MTJ element, and as such has outward facing and inward facing surfaces, where the outward facing surface is facing away from the MTJ element and the inward facing surface is facing towards the MTJ element.

In certain embodiments, the first and second electrodes are arranged such that the facing surfaces of the extending portions of the first and second electrodes are non-overlapping. By facing surfaces is meant that the inward facing surface of the first electrode and the inward facing surface of the second electrode, e.g., the surfaces of the first and second electrodes that are facing towards the MTJ element, respectively. By non-overlapping is meant that the facing surface of the extending portion of the first electrode is not positioned above (or below) the opposing facing surface of the extending portion of the second electrode. Stated another way, non-overlapping electrodes include embodiments where a line normal to and passing through the extending portion of the first electrode does not pass though the extending portion of the second electrode.

As such, in embodiments where the facing surfaces of the extending portions of the first and second electrode do not substantially overlap, the first and second electrodes may extend from their respective edges of the MTJ element in different directions. For instance, as viewed from above, the first electrode may extend from the top surface of the MTJ element towards the left, and the second electrode may extend from the bottom surface of the MTJ element towards the right. Other arrangements of the electrodes are also possible as long as the extending portions of the first and second electrodes are substantially non-overlapping as described above.

In certain embodiments, the electrode may be aligned with the edge of the MTJ element. For instance, a non-overlapping electrode may extend beyond an edge of the MTJ element as described above. In some cases, the edge of the electrode opposite the extending portion may be substantially aligned with the edge of the MTJ element. In some cases, the edge of the electrode is not aligned with the edge of the MTJ element. For example, as described above, the electrode may contact less than the entire surface of the MTJ element, and as such may not extend all the way to the edges of the surface of the MTJ element. Stated another way, in some cases, the electrode may have an end portion that contacts the surface of the MTJ element, but leaves a portion of the surface of the MTJ element un-contacted, such that there is a gap between the edge of the end portion of the electrode and one or more edges of the MTJ element (e.g., one or more edges where the electrode does not extend from). In embodiments where the edge of the electrode is aligned with the edge of the MTJ element or where there is a gap between the edge of the electrode and the edge of the MTJ element as described above, this may facilitate providing a magnetic sensor where the first and second electrodes do not substantially overlap.

Magnetic Sensor Devices

Aspects of the present disclosure include magnetic sensor devices. The magnetic sensor device includes a support. In some embodiments, the support includes an array of magnetic sensors (e.g., an array of biosensors) disposed thereon. In certain embodiments, each magnetic sensor includes one or more magnetic sensor elements (e.g., magnetic tunnel junction (MTJ) elements, also referred to herein as MTJ magnetoresistive elements). Aspects of the magnetic sensors and MTJ elements are described further in the following sections.

In certain embodiments, a magnetic sensor includes two or more MTJ elements. In some cases, the MTJ elements are electrically connected to each other. In certain cases, the MTJ elements are electrically connected to each other in series. For example, the MTJ elements may be electrically connected to each other in series by the first and second electrodes. In some embodiments, by electrically connecting the MTJ elements together in series, a current (e.g., a sense current) may flow through the MTJ elements in series (e.g., sequentially). For example, a minimum arrangement of two MTJ elements in series may include a first electrode, which is electrically connected to a first MTJ element, which is electrically connected to a second electrode, which is electrically connected to a second MTJ element, which is electrically connected to a third electrode. As such, a current may be applied to a first electrode, flow through the first electrode to the first MTJ element, flow through the first MTJ element to the second electrode on an opposing surface of the first MTJ element, flow through the second electrode to the second MTJ element, flow through the second MTJ element to the third electrode on an opposing surface of the second MTJ element. See, e.g., FIG. 2(a). The current may subsequently flow through the third electrode to one or more MTJ elements in series, or to a processor for signal processing, as described herein.

Figure 2:
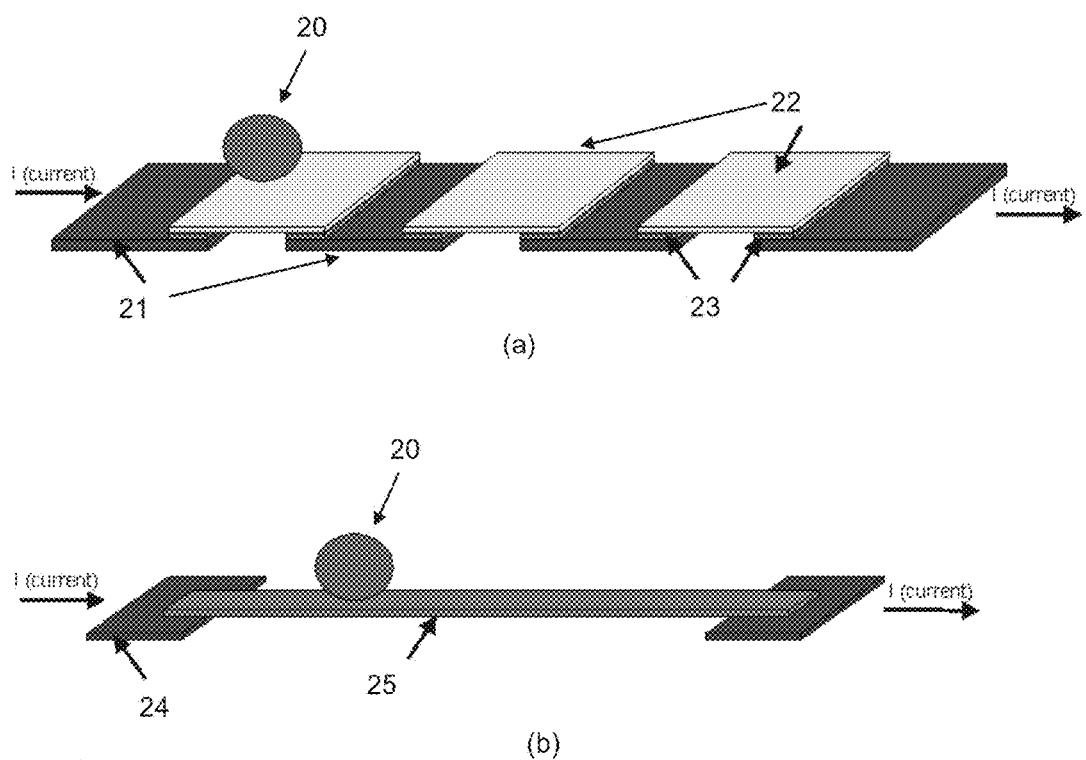
FIGS. 2(a) and 2(b) show schematic drawings of a Magneto Tunnel Junction sensor design (FIG. 2(a)), according to embodiments of the present disclosure vs. existing GMR Spin Valve sensor design (FIG. 2(b)). The sense current passes vertically through a Magneto Tunnel Junction.

FIGS. 2(a) and 2(b) show schematic drawings of an array of MTJ elements arranged in series (FIG. 2(a)), and a GMR spin valve sensor design (FIG. 2(b)). FIGS. 2(a) and 2(b) show magnetic particles (20) on surfaces of the sensors. FIG. 2(a) shows an array of MTJ elements, where the array of MTJ elements include bottom electrodes (21), top electrodes (22), and MTJ elements (23) between the bottom and top electrodes. FIG. 2(b) shows a GMR spin valve sensor design that includes a bottom electrode (24) and a GMR spin valve sensor element (25).

As described above, the electrodes (e.g., first and second electrodes) may contact opposing sides of the MTJ element. As such, the elements of the magnetic sensor (e.g., the MTJ element and two electrodes) may be arranged in a current-perpendicular-to-plane configuration. In the current-perpendicular-to-plane (CPP) configuration, the current is passed through the sensor perpendicular to the layers of the MTJ element, and the electrodes are located on opposing sides of the MTJ element.

In certain embodiments, an array of MTJ elements includes a plurality of MTJ elements arranged in series may include two or more MTJ elements, including 3 or more, 4 or more, 6 or more, 8 or more, 10 or more, 15 or more, 20 or more, 25 or more, 30 or more, 40 or more, 50 or more, 75 or more, 100 or more, 125 or more, 150 or more, 175 or more, 200 or more, 225 or more, or 250 or more magnetic sensors arranged in series. In some cases, the array of MTJ elements includes 100 or more MTJ elements arranged in series.

In some instances, the MTJ elements are arranged (e.g., arranged in series as described above) such that the distance between adjacent electrodes is 50 µm or less, such as 40 µm or less, including 30 µm or less, or 20 µm or less, or 10 µm or less, or 5 µm or less, or 4 µm or less, or 3 µm or less, or 2 µm or less, or 1 µm or less. In some cases, the distance between adjacent electrodes is 2 µm. For example, the distance between adjacent bottom electrodes may be 2 µm. In some cases, the distance between adjacent electrodes is 1 µm. For example, the distance between adjacent top electrodes may be 1 µm.

In certain embodiments, an electrode may have dimensions in the range of 2 µm×2 µm to 200 µm×200 µm, including dimensions of 2 µm×200 µm or less, such as 100 µm×2 µm or less, for instance 2 µm×100 µm or less, or 100 µm×100 µm or less, or 10 µm×10 µm or less, or 5 µm×5 µm or less, or 3 µm×3 µm or less, or 2 µm×2 µm or less, or 1 µm×1 µm or less. In some instances, an electrode (e.g., a top electrode) has dimensions of 150 µm×10 µm or less, or 120 µm×5 µm or less, or 120 µm×2.8 µm or less, or 100 µm×2.8 µm or less, or 75 µm×2.8 µm or less, or 50 µm×2.8 µm or less, or 25 µm×2.8 µm or less, or 10 µm×2.8 µm or less, such as 2.0 µm×2.8 µm. In some instances, an electrode (e.g., a bottom electrode) has dimensions of 150 µm×10 µm or less, or 125 µm×5 µm or less, or 124 µm×2.6 µm or less, or 100 µm×2.6 µm or less, or 75 µm×2.6 µm or less, or 50 µm×2.6 µm or less, or 25 µm×2.6 µm or less, or 10 µm×2.8 µm or less, such as 6.8 µm×2.6 µm.

In certain embodiments, an electrode is composed of an electrically conductive material. In some cases, the electrode is made of a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like. In some instances, the electrode is made of tantalum. In some instances, the electrode is made of ruthenium. In some instances, the electrode includes a layer of an electrically conductive material as described above. For example, the electrode may include a layer of a conductive metal, such as tantalum. In some instances, the electrode includes two or more layers of electrically conductive materials as described above. For example, the electrode may include alternating layers of two different conductive metals, such as tantalum and ruthenium. In some instances, the thickness of the electrode ranges from 1 nm to 1000 nm, such as from 1 nm to 500 nm, or 1 nm to 250 nm, or 1 nm to 100 nm, or 1 nm to 75 nm, or 1 nm to 50 nm, or 1 nm to 45 nm, or 1 nm to 40 nm, or 1 nm to 35 nm, or 1 nm to 30 nm, or 1 nm to 25 nm, or 1 nm to 20 nm, or 1 nm to 15 nm, or 1 nm to 10 nm, or 1 nm to 5 nm. In some embodiments, the thickness of the electrode ranges from 1 nm to 30 nm, such as a thickness of 30 nm, or 20 nm, or 10 nm.

In certain embodiments, a magnetic sensor includes a plurality of MTJ elements. In some cases, the magnetic sensor includes two or more MTJ elements (e.g., two or more MTJ elements arranged in series), as described above. In some instances, the magnetic sensor device includes MTJ elements arranged in series and additional MTJ elements electrically connected in parallel to the first series of MTJ sensor arrays. The additional MTJ elements may include two or more MTJ elements arranged in series as described above. As such, in certain cases, the magnetic sensor may include an arrangement of MTJ elements where a plurality of MTJ elements are electrically connected both in series and in parallel.

Aspects of the present disclosure include a magnetic sensor device, where the magnetic sensor device includes a support. In some embodiments, the support includes an array of magnetic sensors (e.g., an array of biosensors) disposed thereon. In certain embodiments, the support has a thickness of 5 mm or less, such as 2 mm or less, including 1.6 mm or less, or 1.0 mm or less, or 0.5 mm or less, or 0.3 mm or less, or 0.2 mm or less. In certain embodiments, the support has a width of 20 mm or less, or 15 mm or less, such as 12 mm or less, including 10 mm or less, or 5 mm or less, or 2 mm or less.

In certain embodiments, the support of the magnetic sensor device is shaped as a rectangular solid (although other shapes are possible), having a length ranging from 1 mm to 20 mm, such as 1 mm to 10 mm, including 1 mm to 5 mm; a width ranging from 1 mm to 20 mm, such as 1 mm to 10 mm, including 1 mm to 5 mm, or 1 mm to 3 mm; and a thickness ranging from 0.1 mm to 5 mm, such as 0.2 mm to 1 mm, including 0.3 mm to 0.5 mm.

Magnetic Sensor Arrays

In certain embodiments, the magnetic sensor device includes an array of magnetic sensors (e.g., an array of biosensors). The array of magnetic sensors may have a variety of different configurations, e.g., with respect to magnetic sensor configuration. In certain embodiments, the subject magnetic sensors are arranged on a biochip (e.g., a biosensor chip). By "biochip" or "biosensor chip" is meant a magnetic sensor device that includes an array of magnetic sensors (e.g., an array of biosensors). For instance, a biochip may include a magnetic sensor device that includes a support surface which displays two or more distinct arrays of magnetic sensors on the support surface. In certain embodiments, the magnetic sensor device includes a support surface with an array of magnetic sensors.

An "array" includes any two-dimensional or substantially two-dimensional (as well as a three-dimensional) arrangement of addressable regions, e.g., spatially addressable regions. An array is "addressable" when it has multiple sensors positioned at particular predetermined locations (e.g., "addresses") on the array. Array features (e.g., sensors) may be separated by intervening spaces. Any given support may carry one, two, four or more arrays disposed on a front surface of the support. Depending upon the use, any or all of the arrays may be the same or different from one another and each may contain multiple distinct magnetic sensors. An array may contain one or more, including 2 or more, 4 or more, 8 or more, 10 or more, 50 or more, 100 or more, 250 or more, 500 or more, 750 or more, 1000 or more magnetic sensors. For example, 64 magnetic sensors can be arranged into an 8×8 array, or 80 magnetic sensors can be arranged in an 8×10 array, or 90 sensors can be arranged in a 9×10 array.

In some instances, the magnetic sensors are arranged in the array in rows and columns of magnetic sensors. For example, an array may include one or more rows of two or more magnetic sensors. In some cases, an array includes 1 or more rows, such as 2 or more, or 3 or more, or 4 or more, or 5 or more, or 6 or more, or 7 or more, or 8 or more, or 9 or more, or 10 or more, or 12 or more, or 14 or more, or 16 or more, or 18 or more, or 20 or more, or 25 or more, or 30 or more, or 35 or more, or 40 or more, or 45 or more, or 50 or more rows of magnetic sensors. In some cases, an array includes 1 or more columns, such as 2 or more, or 3 or more, or 4 or more, or 5 or more, or 6 or more, or 7 or more, or 8 or more, or 9 or more, or 10 or more, or 12 or more, or 14 or more, or 16 or more, or 18 or more, or 20 or more, or 25 or more, or 30 or more, or 35 or more, or 40 or more, or 45 or more, or 50 or more columns of magnetic sensors. For example, 64 magnetic sensors can be arranged into an 8×8 array that includes 8 rows and 8 columns of magnetic sensors, or 80 magnetic sensors can be arranged in an 8×10 array that includes 10 rows and 8 columns of magnetic sensors. See, e.g., FIG. 8, and FIG. 9.

In certain embodiments, the magnetic sensors can be arranged into an array with an area of 10 cm$^2$ or less, or 9 cm$^2$ or less, 5 cm$^2$ or less, 4 cm$^2$ or less, e.g., 2 cm$^2$ or less, 1.2 cm$^2$ or less, 0.1 cm$^2$ or less, including 50 mm$^2$ or less, 20 mm$^2$ or less, such as 10 mm$^2$ or less, or even smaller. For example, the magnetic sensors can be arranged into an array with an area of 15 mm$^2$ or less, such as 12.2 mm$^2$ or less (e.g., 3.2 mm×3.8 mm). In some instances, the magnetic sensors are arranged into an array with an area of 20 mm$^2$. For instance, the magnetic sensors may have a density in an array of 1 magnetic sensor per 2 mm$^2$ array area or less, such as 1 magnetic sensor per 1 mm$^2$ array area or less, or 1 magnetic sensor per 0.5 mm$^2$ array area, or 1 magnetic sensor per 0.2 mm$^2$ array area, or 1 magnetic sensor per 0.16 mm$^2$ array area, or 1 magnetic sensor per 0.14 mm$^2$ array area, or 1 magnetic sensor per 0.12 mm$^2$ array area, or 1 magnetic sensor per 0.1 mm$^2$ array area, or 1 magnetic sensor per 0.08 mm$^2$ array area, or 1 magnetic sensor per 0.05 mm$^2$ array area. In some cases, the magnetic sensors may have a density in an array of 1 magnetic sensor per 0.16 mm$^2$ array area.

In some embodiments, magnetic biosensors with multiple MTJ elements, according to the embodiments of the present disclosure, are dimensioned to cover a portion of the support which is contacted with a sample of biological molecules during an assay. The placement of the sample (e.g., biological molecules) onto individual sensors may be performed by placing small droplets of a liquid sample with biological molecules onto certain regions of the support, or by placing a stamp coated with biological molecules into contact with the support. In some embodiments, the area of the support coated by a sample of biological molecules and the area of a biosensor are substantially similar. For example, the biosensor may have dimensions in the range of 10 µm×10 µm to 1000 µm×1000 µm, including dimensions of 10 µm×1000 µm or less, such as 1000 µm×10 µm or less, for instance 800 µm×800 µm or less, or 400 µm×400 µm or less, or 200 µm×200 µm or less, or 180 µm×180 µm or less, or 160 µm×160 µm or less, or 140 µm×140 µm or less, or 120 µm×120 µm or less, or 100 µm×100 µm or less, or 80 µm×80 µm or less, or 50 µm×50 µm or less, or 30 µm×30 µm or less. In some instances, a biosensor has dimensions of 140 µm×140 µm or less, such as 120 µm×120 µm.

In some embodiments, magnetic biosensors with multiple MTJ elements, according to the embodiments of the present disclosure, are spaced apart such that the number of biosensors per unit area is maximized, while still allowing individual biosensors to be contacted with separate droplets of a liquid sample containing biological molecules. To achieve substantial separation between adjacent droplets of liquid placed onto individual biosensors, the biosensors may be spaced a certain distance apart. In some instances, the intervening spaces between adjacent biosensors are an inert, non-sensing area between adjacent biosensors. In some embodiments, this inert area between adjacent biosensors may cover a distance of 1 to 5 times the size of the biosensors. For example, if the biosensor covers an area of 100 µm×100 µm, then the inert area between adjacent biosensors may cover a distance ranging from 100 µm to 500 µm. As discussed above, in some instances, the biosensors have dimensions of 120 µm×120 µm. In some embodiments, the biosensors may be arranged in regular intervals of 400 µm (as measured from the center of a biosensor to the center of the adjacent biosensor), so that the inert space between adjacent biosensors is approximately 280 µm in length.

In certain embodiments, at least some, or all, of the magnetic sensors have an analyte-specific probe (e.g., a surface capture ligand) stably associated with a surface of the sensor. For example, each magnetic sensor array may include one or more magnetic sensors having an analyte-specific probe bound to a surface of the magnetic sensor. Where a given array includes two or more magnetic sensors, each sensor may have the same or different analyte-specific probe associated with its surface. For example, a magnetic sensor array may include two or more distinct magnetic sensors each configured to specifically detect the same analyte. In some cases, different analyte-specific probes may be present on the sensor surfaces of such devices, such that each different analyte-specific probe specifically binds to a distinct analyte. For instance, a magnetic sensor array may include two or more distinct magnetic sensors each configured to specifically detect a different analyte. In other cases, the magnetic sensor devices include magnetic sensors that are free of any analyte-specific probes, such that the surface of the magnetic sensor is functionalized to bind directly to the analyte. In some instances, the magnetic sensor includes a blocking layer disposed over the surface of the magnetic sensor. The blocking layer may be configured to inhibit the binding of any analyte-specific probes or analyte to the surface of the magnetic sensor (e.g., where such blocked magnetic sensors may serve as sources of reference or control electrical signals).

As described above, in certain embodiments, the magnetic sensor device includes two or more magnetic sensor arrays disposed on a substrate. As such, the magnetic sensor device includes two or more magnetic sensor arrays. As described above, each magnetic sensor array may have one or more magnetic sensors with each magnetic sensor configured to detect the same or different analytes. Thus, each magnetic sensor array on the magnetic sensor device may be configured to detect the same set or different sets of analytes. For example, a magnetic sensor device may include two or more distinct magnetic sensor arrays each configured to specifically detect the same set of analytes. In other cases, a magnetic sensor device may include two or more distinct magnetic sensors each configured to specifically detect a different set of analytes.

In certain embodiments, areas in between the magnetic sensors in an array may be present which do not carry any analyte-specific probes or are not functionalized to bind directly to the analyte. Such inter-sensor areas, when present, may be of various sizes and configurations. In some instances, these inter-sensor areas may be configured to inhibit or prevent fluid movement among different sensors, e.g., where the inter-sensor areas are coated with hydrophobic materials and/or fluid barriers, such as walls.

Electronic communication elements, e.g., conductive leads, may be present which are configured to electronically couple the magnetic sensors to components of the system, such as processors, displays, etc. Additionally, a given magnetic sensor device may include a variety of other components in addition to the magnetic sensor array. Additional magnetic sensor device components may include, but are not limited to: signal processing components, power sources, fluid handling components, wired or wireless communication components, etc.

In certain embodiments, the magnetic sensor device is configured to produce a detectable signal from a minimum amount of sample. In some instances, the magnetic sensor device is configured to produce a detectable signal from a sample size of 10 mL or less, or 5 mL or less, or 3 mL or less, or 1 mL or less, such as 500 µL or less, including 100 µL or less, for example 50 µL or less, or 25 µL or less, or 10 µL or less. As such, in some cases, the fluid reservoirs of the reservoir plate may be configured to receive a minimum amount of sample needed to produce a detectable signal. For example, the fluid reservoirs may be configured to receive a sample of 10 mL or less, or 5 mL or less, or 3 mL or less, or 1 mL or less, such as 500 µL or less, including 100 µL or less, for example 50 µL or less, or 25 µL or less, or 10 µL or less, or 5 µL or less, or 1 µL or less.

In some embodiments, the magnetic sensor device is configured to connect to a system for detecting the presence of an analyte in a sample. Accordingly, in certain embodiments, the magnetic sensor device does not include a magnetic field source. The magnetic field source may be included in the system for detecting the presence of an analyte in the sample and, thus not included in the magnetic sensor device. Thus, the assay protocol may include operably coupling the magnetic sensor device to the system for detecting the presence of an analyte in the sample. In some instances, the magnetic sensor device may be operably coupled to an activation and signal processing unit of the system, as described herein. The magnetic sensor device may include one or more electrical contacts configured to electrically connect the magnetic sensor device to the system, such as to the activation and signal processing unit of the system. The electrical contacts may be arranged along an edge of the magnetic sensor device.

In certain embodiments, the magnetic sensor device includes a programmable memory. In some cases, the programmable memory is configured to store information, such as information including, but not limited to: calibration data (e.g., calibration data for each magnetic sensor and/or each magnetic sensor array); a record of how the magnetic sensors have been prepared with surface functionalization molecules prior to the assay; a record of completed assay steps; a record about which sample was measured; a record of the measurement results; and the like. In some instances, a barcode may be used instead of, or in addition to, the programmable memory. In embodiments of the magnetic sensor device that include a barcode, information associated with the magnetic sensor device may be stored and retrieved from an information system separate from the magnetic sensor device, such as the activation and signal processing unit of the system.

Magnetic Sensors

As described above, each magnetic sensor may include one or more MTJ sensor elements. In some cases, magnetic sensors are sensors configured to detect the presence of nearby magnetic labels without any direct physical contact between the magnetic sensor and the magnetic label. In certain embodiments, the magnetic sensors are configured to detect the presence of an analyte in a sample. For example, a magnetic label may be bound, either directly or indirectly, to an analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

In some instances, the magnetic sensors have a detection range from 1 nm to 1000 nm from the surface of the magnetic sensor, such as from 1 nm to 800 nm, including from 1 nm to 500 nm, such as from 1 nm to 300 nm, including from 1 nm to 100 nm from the surface of the magnetic sensor. In some instances, a minimization of the detection range of the sensors may facilitate detection of specifically bound analytes while minimizing detectable signals from analytes not of interest. By "detection range" is meant the distance from the surface of the magnetic sensor where the presence of a magnetic label will induce a detectable signal in the magnetic sensor. In some cases, magnetic labels positioned close enough to the surface of the magnetic sensor to be within the detection range of the magnetic sensor will induce a detectable signal in the magnetic sensor. In certain instances, magnetic labels positioned at a distance from the surface of the magnetic sensor that is greater than the detection range of the magnetic sensor will not induce a detectable or non-negligible signal in the magnetic sensor. For example, a magnetic label may have a magnetic flux that is proportional to $1/r^3$, where r is the distance between the magnetic sensor and the magnetic label. Thus, only those magnetic labels that are positioned in close proximity (e.g., within the detection range of the magnetic sensor) will induce a detectable signal in the magnetic sensor.

In certain embodiments, the surface of the magnetic sensor is functionalized to bind directly to an analyte. For example, the surface of the magnetic sensor may be functionalized to provide for covalent binding or non-covalent association of the analyte and magnetic sensor, including, but not limited to, non-specific adsorption, binding based on electrostatic interactions (e.g., ion-ion pair interactions), hydrophobic interactions, hydrogen bonding interactions, and the like.

In some instances, the surface of the magnetic sensor includes an analyte-specific probe (e.g., a surface capture ligand) that specifically binds to an analyte. The analyte-specific probe may be bound to the surface of the magnetic sensor. For instance, a cationic polymer such as polyethyleneimine (PEI) can be used to nonspecifically bind charged antibodies to the sensor surface via physiabsorption. Alternatively, a covalent chemistry can be used utilizing free amines or free thiol groups on the analyte-specific probe to covalently bind the analyte-specific probe to the surface of the magnetic sensor. For example, an N-hydroxysuccinimide (NHS) to 1-ethyl-3-(3-dimethylaminopropyl) carbodiimide (EDC) coupling system may be used to covalently bind the analyte-specific probe to the surface of the magnetic sensor.

The analyte-specific probe may include one member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like. In certain embodiments, the surface of the magnetic sensor includes an antibody that specifically binds to an analyte of interest. Accordingly, contacting the magnetic sensor with an assay composition that includes the analyte of interest may result in binding of the analyte to the analyte-specific probe (e.g., antibody) bound to the surface of the magnetic sensor.

In certain embodiments, the magnetic sensor is configured to generate an electrical signal in response to a magnetic label in proximity to a surface of the magnetic sensor. For example, the magnetic sensors may be configured to detect changes in the resistance of the magnetic sensor induced by changes in the local magnetic field. In some cases, binding of a magnetic label (e.g., a magnetic nanoparticle label) in close proximity to the magnetic sensor, as described above, induces a detectable change in the resistance of the magnetic sensor. For instance, in the presence of an applied external magnetic field, the magnetic labels near the magnetic sensor may be magnetized. The local magnetic field of the magnetized magnetic labels may induce a detectable change in the resistance of the underlying magnetic sensor. Thus, the presence of the magnetic labels can be detected by detecting changes in the resistance of the magnetic sensor. In certain embodiments, the magnetic sensors are configured to detect changes in resistance of 1 Ohm or less, such as 500 mOhm or less, including 100 mOhm or less, or 50 mOhm or less, or 25 mOhm or less, or 10 mOhm or less, or 5 mOhm or less, or 1 mOhm or less. In certain embodiments, the change in resistance may be expressed in parts per million (PPM) relative to the original sensor resistance, such as a change in resistance of 2 PPM or more, or 20 PPM or more, or 200 PPM or more, or 400 PPM or more, or 600 PPM or more, or 1000 PPM or more, or 2000 PPM or more, or 4000 PPM or more, or 6000 PPM or more, or 10,000 PPM or more, or 20,000 PPM or more, or 40,000 PPM or more, or 60,000 PPM or more, or 100,000 PPM or more, or 200,000 PPM or more.

In certain cases, the magnetic sensor is a multilayer thin film structures. The sensors may include alternating layers of a ferromagnetic material and a non-magnetic material. The ferromagnetic material may include, but is not limited to, Permalloy (NiFe), iron cobalt (FeCo), nickel iron cobalt (NiFeCo), nickel oxide (NiO), cobalt oxide (CoO), nickel cobalt oxide (NiCoO), ferric oxide ($Fe_2O_3$), CoFeB, Ru, PtMn, combinations thereof, and the like. In some cases, the non-magnetic material is an insulating layer, such as, but not limited to, MgO, alumina, and the like. In certain embodiments, the ferromagnetic layers have a thickness of 1 nm to 10 nm, such as 2 nm to 8 nm, including 3 nm to 4 nm. In some instances, the non-magnetic layer has a thickness of 0.2 nm to 5 nm, such as 1 nm to 3 nm, including 1.5 nm to 2.5 nm, or 1.8 nm to 2.2 nm.

Magnetic Tunnel Junction (MTJ) Magnetoresistive Elements

In certain embodiments, the magnetic sensor includes a magnetic tunnel junction (MTJ) magnetoresistive element (also referred to herein as an MTJ element). In some cases, the MTJ element includes a multilayer structure that includes a first ferromagnetic layer, an insulating layer disposed on the first ferromagnetic layer, and a second ferromagnetic layer disposed on the insulating layer. The insulating layer may be a thin insulating tunnel barrier, and may include alumina, MgO, and the like. In some cases, electron tunneling between the first and the second ferromagnetic layers depends on the relative magnetization of the two ferromagnetic layers. For example, in certain embodiments, the tunneling current is high when the magnetization vectors of the first and second ferromagnetic layers are parallel and the tunneling current is low when the magnetization vectors of the first and second ferromagnetic layers antiparallel.

In some instances, MTJ elements have a magnetoresistance ratio (MR) of 1% to 300%, such as 10% to 250%, including 25% to 200%. Changes in the resistance of the MTJ element due to the presence of magnetic labels near the surface of the MTJ element may be detected, as described above. In some instances, the MTJ elements have an MR of 50% or more, or 75% or more, or 100% or more, or 125% or more, or 150% or more, or 175% or more, or 200% or more, or 225% or more, or 250% or more, or 275% or more, or 200% or more. For instance, the MTJ element may have an MR of 225% or more.

In certain embodiments, the second ferromagnetic layer (e.g., the layer of the MTJ element positioned at the surface of the MTJ element) includes two of more layers. For example, the second ferromagnetic layer may include a first layer, a second layer disposed on the first layer, and a third layer disposed on the second layer. In some cases, the first layer is a thin ferromagnetic layer (e.g., NiFe, CoFe, CoFeB, and the like). The thin metallic layer may have a thickness of 6 nm or less, such as 5 nm or less, including 4 nm or less, 3 nm or less, 2 nm or less, or 1 nm or less, or 0.5 nm or less. The second layer may include a conductive metal, e.g., copper, aluminum, palladium, a palladium alloy, a palladium oxide, platinum, a platinum alloy, a platinum oxide, ruthenium, a ruthenium alloy, a ruthenium oxide, silver, a silver alloy, a silver oxide, tin, a tin alloy, a tin oxide, titanium, a titanium alloy, a titanium oxide, tantalum, a tantalum alloy, a tantalum oxide, combinations thereof, and the like. The second layer may have a thickness of 2 nm or less, such as 0.5 nm or less, including 0.4 nm or less, 0.3 nm or less, 0.2 nm or less, or 0.1 nm or less. The third layer may include a ferromagnetic material such as, but not limited to, NiFe, CoFe, CoFeB, and the like. The third layer may have a thickness of 6 nm or less, such as 5 nm or less, including 4 nm or less, 3 nm or less, 2 nm or less, or 1 nm or less, or 0.5 nm or less.

In some cases, the MTJ element is configured such that the distance between an associated magnetic label and the top surface of the free layer ranges from 5 nm to 1000 nm, or 10 nm to 800 nm, such as from 20 nm to 600 nm, including from 40 nm to 400 nm, such as from 60 nm to 300 nm, including from 80 nm to 250 nm.

The MTJ element may include a passivation layer disposed on one or more of the MTJ element surfaces. In some instances, the passivation layer has a thickness of 60 nm or less, such as 50 nm or less, including 40 nm or less, 30 nm or less, 20 nm or less, 10 nm or less. For example, the passivation layer may have a thickness of 1 nm to 50 nm, such as from 1 nm to 40 nm, including from 1 nm to 30 nm, or form 1 nm to 20 nm. In some instances, the passivation layer has a thickness of 30 nm. In some cases, the passivation layer includes gold, tantalum, a tantalum alloy, a tantalum oxide, aluminum, an aluminum alloy, an aluminum oxide, $SiO_2$, $Si_3N_4$, $ZrO_2$, combinations thereof, and the like. In certain embodiments, a passivation layer with a thickness as described above facilitates a maximization in signal detected from magnetic labels specifically bound to the sensor surface while minimizing the signal from magnetic labels that are not specifically bound.

In certain embodiments, a MTJ element has dimensions ranging from 1 μm×1 μm to 200 μm×200 μm, including dimensions of 1 μm×200 μm or less, such as 200 μm×1 μm or less, for instance 150 μm×10 μm or less, or 120 μm×5 μm or less, or 120 μm×0.8 μm or less, or 0.8 μm×120 μm or less, or 100 μm×0.7 μm or less, or 100 μm×0.6 μm or less, or 100 μm×0.5 μm or less, or 10 μm×0.6 μm or less, or 10 μm×0.5 μm or less. In some instances, a MTJ element has dimensions of 120 μm×0.8 μm or less, such as 2.0 μm×0.8 μm.

Magnetic tunnel junction (MTJ) detectors are further described in U.S. Ser. No. 12/234,506, filed Sep. 19, 2008, and entitled "Analyte Detection with Magnetic Sensors", the disclosure of which is hereby incorporated by reference in its entirety. Detectors are further described in U.S. patent application Ser. No. 10/829,505, filed Apr. 22, 2004 and entitled "Magnetic nanoparticles, magnetic detector arrays, and methods for their use in detecting biological molecules", the disclosure of which is hereby incorporated by reference in its entirety.

Magnetic Sensing Areas

In certain embodiments, the magnetic sensor device may be configured to include one or more magnetic sensing areas. A magnetic sensing area may correspond to the area of the device where an array of magnetic sensors (e.g., an array of biosensors) is positioned. For instance, the magnetic sensing area may be an area on the surface of the device that is exposed to the sample during use, and which has an array of magnetic sensors (e.g., an array of biosensors) as described above.

The magnetic sensing area may be configured to include a fluid reservoir. The fluid reservoir may be any of a variety of configurations, where the fluid reservoir is configured to hold a sample in contact with the magnetic sensor arrays. Accordingly, configurations of the fluid reservoirs may include, but are not limited to: cylindrical well configurations, square well configurations, rectangular well configurations, round bottom well configurations, and the like. For instance, the fluid reservoirs may include walls that separate one fluid reservoir from adjacent fluid reservoirs. The walls may be substantially vertical with respect to the surface of the reservoir plate. In some cases, the walls of each fluid reservoir define a volume of space that may receive a volume of sample equal to or less than the volume of space defined by the fluid reservoir.

In certain embodiments, a fluid reservoir has a volume of 10 mL or less, or 5 mL or less, or 3 mL or less, or 1 mL or less, such as 500 μL or less, including 100 μL or less, for example 50 μL or less, or 25 μL or less, or 10 μL or less, which is sufficient to contain a sample volume of an equal or lesser volume.

Magnetic Sensor Systems

In certain embodiments, the systems include a magnetic sensor device, and a magnetic field source. The magnetic sensor device includes a support having two or more arrays of magnetic sensors (e.g., arrays of biosensors) positioned thereon. The system may be configured to obtain signals from each array of magnetic sensors indicating whether one or more analytes is present in each sample.

In certain embodiments, the system includes a magnetic field source. The magnetic field source may be configured to apply a magnetic field to the magnetic sensor device (e.g., the magnetic sensor arrays) sufficient to produce a DC and/or AC field in the assay sensing area (e.g. in the area where the magnetic sensor arrays are positioned during signal acquisition). In some instances, the magnetic field source is configured to produce a magnetic field with a magnetic field strength of 1 Oe or more, or 5 Oe or more, or 10 Oe or more, or 20 Oe or more, or 30 Oe or more, or 40 Oe or more, or 50 Oe or more, or 60 Oe or more, or 70 Oe or more, or 80 Oe or more, or 90 Oe or more, or 100 Oe or more.

The magnetic field source may be positioned such that a magnetic field is produced in the area where the magnetic sensor arrays are positioned when the magnetic sensor device is in use. In some cases, the magnetic field source is configured to generate a uniform, controllable magnetic field around the set of fluid reservoirs on the reservoir plate where an assay is being performed. The magnetic field source may include one or more, such as two or more, three or more, four or more magnetic field generating components. In some cases, the magnetic field source may include one or more electromagnets, such as coil electromagnets. The coil electromagnets may include wire-wound coils. For example, the magnetic field source may include two electromagnets arranged in a Helmholtz coil geometry.

Embodiments of the systems further include computer-based systems. The systems may be configured to qualitatively and/or quantitatively assess binding interactions as described above. A "computer-based system" refers to the hardware, software, and data storage components used to analyze the signals from the magnetic sensors. The hardware of the computer-based systems may include a central processing unit (CPU), inputs, outputs, and data storage components. Any of a variety of computer-based systems is suitable for use in the subject systems. The data storage components may include any computer readable medium that includes a device for recording signals from the magnetic sensor arrays, or an accessible memory component that can store signals from the magnetic sensor arrays.

To "record" data, programming or other information on a computer readable medium refers to a process for storing information, using any such methods as known in the art. Any convenient data storage structure may be chosen, depending on the method used to access the stored information. A variety of data processor programs and formats can be used for storage, e.g. word processing text file, database format, etc.

In certain embodiments, the system includes an activation and signal processing unit. The activation and signal processing unit may be configured to operably couple to the magnetic sensor device. In some instances, the activation and signal processing unit is electrically coupled to the magnetic sensor device. The activation and signal processing unit may be electrically coupled such as to provide bi-directional communication to and from the magnetic sensor device. For example, the activation and signal processing unit may be configured to provide power, activation signals, etc. to components of the magnetic sensor device, such as, but not limited to the magnetic sensor arrays. As such, the activation and signal processing unit may include an activation signal generator. The activation signal generator may be configured to provide power, activation signals, etc. to components of the analyte detection device, such as, but not limited to the magnetic sensor arrays. In some instances, the activation and signal processing unit is configured to apply a voltage across the magnetic sensor arrays ranging from 1 mV to 10 V, such as 100 mV to 5 V, including 200 mV to 1 V, for example, 300 mV to 500 mV. In some cases, the activation and signal processing unit is configured to apply a voltage across the magnetic sensor arrays of 500 mV.

Additionally, the activation and signal processing unit may be configured to receive signals from the magnetic sensor device, such as from the magnetic sensor arrays of the magnetic sensor device. The signals from the magnetic sensor arrays of the magnetic sensor device may be used to detect the presence of one or more analytes in the samples. In some instances, the activation and signal processing unit may include a processor configured to output an analyte detection result in response to receiving signals from the magnetic sensor arrays. Thus, the processor of the activation and signal processing unit may be configured to receive signals from the magnetic sensor device, process the signals according to a predetermined algorithm, obtain a result related to the presence of one or more analytes in the samples, and output the result to a user in a human-readable or an audible format.

A "processor" references any hardware and/or software combination that will perform one or more programmed functions. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid-state device based). For example, a magnetic medium, optical disk or solid-state memory device may carry the programming, and can be read by a suitable reader communicating with the processor.

In some instances, the subject systems are configured to modulate the current applied to the magnetic sensor arrays (e.g., the sense current). The subject systems may also be configured to modulate the magnetic field generated by the magnetic field source. Modulating the sense current and the magnetic field may facilitate a minimization in signal noise, and thus a maximization in the signal to noise ratio. Additional aspects of modulating the sense current and the magnetic field are described in more detail in U.S. application Ser. No. 12/759,584, entitled "Methods and Devices for Detecting the Presence of an Analyte in a Sample, filed on Apr. 13, 2010, the disclosure of which is incorporated herein by reference in its entirety.

Embodiments of the subject systems may also include the following components: (a) a wired or wireless communications module configured to transfer information between the system and one or more users, e.g., via a user computer, as described below; and (b) a processor for performing one or more tasks involved in the qualitative and/or quantitative analysis of the signals from the magnetic sensors. In certain embodiments, a computer program product is provided that includes a computer-usable medium having control logic (e.g., a computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the magnetic sensor device and activation and signal processing unit, the systems may include a number of additional components, such as, but not limited to: data output devices, e.g., monitors, speakers, etc.; data input devices, e.g., interface ports, buttons, switches, keyboards, etc.; fluid handling components, e.g., microfluidic components; power sources; power amplifiers; wired or wireless communication components; etc. For example, the systems may include fluid handling components, such as microfluidic fluid handling components. In certain embodiments, the microfluidic fluid handling components are configured to deliver a fluid to the fluid reservoirs of the reservoir plate. In some cases, the fluid includes one or more of the following: an assay composition, a sample, a magnetic label, a capture probe, a reagent, and the like. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less.

In certain embodiments, the system is a high-sensitivity analyte detector. By "high-sensitivity" is meant that the system is configured to detect an analyte in a sample, where the concentration of the analyte in the sample is low. In some cases, the system is configured to produce a detectable signal indicating the presence of an analyte of interest in a sample where the concentration of the analyte in the sample is 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less. Stated another way, the system may be configured to have a detection limit, e.g., a lower limit of quantitation (LLOQ), of 1 µM or less, such as 100 nM or less, or 10 nM or less, or 1 nM or less, including 100 pM or less, or 10 pM or less, or 1 pM or less, for example 500 fM or less, or 250 fM or less, or 100 fM or less, or 50 fM or less, or 25 fM or less, such as 10 fM or less, or 5 fM or less, or 1 fM or less.

In certain embodiments, the systems include a display. The display may be configured to provide a visual indication of an analyte detection result obtained from the activation and signal processing unit, as described above. The display may be configured to display a qualitative analyte detection result. For instance, the qualitative display may be configured to display qualitative indicators to a user that a sample includes or does not include a specific analyte of interest. In some embodiments, the display may be configured to display an analyte detection result, where the analyte detection result is a quantitative result, e.g., a quantitative measurement of the concentration of an analyte in a sample. For example, in embodiments where the system is configured to output a quantitative analyte detection result, the system may include a display configured to display the quantitative analyte detection result.

The magnetic sensor device optionally includes a programmable memory, which prior to and during the use of the magnetic sensor device can be programmed with relevant information such as: calibration data for each individual sensor; a record of how the biochip has been prepared with surface functionalization molecules prior to the assay; a record of all completed assay steps; a record about which sample was measured; a record of the measurement results; and the like.

Methods

Aspects of the present disclosure also include a method for evaluating whether an analyte is present in a sample. The method includes contacting a magnetic sensor device with a set of samples contained in a set of fluid reservoirs to generate a signal. In addition, the method includes evaluating whether the analyte is present in each sample based on the signal.

Embodiments of the methods are directed to evaluating whether an analyte is present in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence of two or more distinct analytes, in which the two or more analytes are different from each other, is determined. For example, analytes may include detectable differences in their molecular structure, sequence, and the like. In some instances, the number of analytes is greater than 2, such as 4 or more, 6 or more, 8 or more, etc., up to 20 or more, e.g., 50 or more, including 100 or more, or 1000 or more distinct analytes. In certain embodiments, the methods include the multiplex analysis of 2 to 1000 distinct analytes, such as 4 to 500 distinct analytes, including 4 to 200 distinct analytes, or 4 to 100 distinct analytes, or 4 to 50 distinct analytes, or 4 to 20 distinct analytes. In certain embodiments, several multiplex assays may be conducted in parallel substantially simultaneously.

In some instances, the methods are wash-free methods of evaluating the presence of one or more analytes in a sample. By "wash-free" is meant that no washing step is performed following reagent and/or sample contact with a sensor surface. As such, no step is performed during the assays of these embodiments in which unbound reagent (e.g., unbound magnetic labels) or unbound sample is removed from the sensor surface. Accordingly, while the methods may include sequential contact of one or more distinct reagents and/or samples to a sensor surface, at no point during the assays is the sample surface contacted with a fluid in a manner that removes unbound reagent or sample from the sensor surface. For example, in certain embodiments, no washing step is performed following contact of the sensor surface with a sample. In some cases, the method does not include a washing step following contact of the sensor with a magnetic label. In certain instances, no washing step is performed following contact of the sensor surface with a capture probe.

In certain embodiments where a wash step is performed, the wash step does not substantially change the signal from the magnetic sensor. The wash step may not result in a substantial change in the signal from the magnetic sensor because, in some instances, unbound magnetic labels do not have a substantially detectable signal as described herein. For example, if a wash step is performed, in some cases, the wash step results in a signal change of 25% or less, such as 20% or less, or 15% or less, or 10% or less or 5% or less, or 4% or less, or 3% or less, or 2% or less, or 1% or less. In some embodiments, the wash step results in a decrease in the signal from the sensor of 25% or less, such as 20% or less, or 15% or less, or 10% or less or 5% or less, or 4% or less, or 3% or less, or 2% or less, or 1% or less.

Aspects of the methods may also include obtaining a real-time signal from the magnetic sensor device. As such, embodiments of the method include obtaining a real-time signal from the magnetic sensor arrays. By "real-time" is meant that a signal is observed as it is being produced or immediately thereafter. For example, a real-time signal is obtained from the moment of its initiation and is obtained continuously over a given period of time. Accordingly, certain embodiments include observing the evolution in real time of the signal associated with the occurrence of a binding interaction of interest (e.g., the binding of the analyte of interest to the magnetic sensor and/or binding of a magnetic label to the analyte of interest). The real-time signal may include two or more data points obtained over a given period of time, where in certain embodiments the signal obtained is a continuous set of data points (e.g., in the form of a trace) obtained continuously over a given period of time of interest. The time period of interest may vary, ranging in some instances from 0.5 min to 60 min, such as 1 min to 30 min, including 1 min to 15 min, or 1 min to 10 min. For example, the time period may begin at the moment of initiation of the real-time signal and may continue until the sensor reaches a maximum or saturation level (e.g., where all the analyte binding sites on the sensor are occupied). For example, in some cases, the time period begins when a sample is contacted with the sensor. In some cases, the time period may begin prior to contacting the sample with the sensor, e.g., to record a baseline signal before contacting sample to the sensor. The number of data points in the signal may also vary, where in some instances, the number of data points is sufficient to provide a continuous stretch of data over the time course of the real-time signal. By "continuous" is meant that data points are obtained repeatedly with a repetition rate of 1 data point per minute or more, such as 2 data points per minute or more, including 5 data points per minute or more, or 10 data points per minute or more, or 30 data points per minute or more, or 60 data points per minute or more (e.g., 1 data point per second or more), or 2 data points per second or more, or 5 data points per second or more, or 10 data points per second or more, or 20 data points per second or more, or 50 data points per second or more, or 75 data points per second or more, or 100 data points per second or more.

In certain embodiments, the real-time signal is a real-time analyte-specific signal. A real-time analyte-specific signal is a real-time signal as described above that is obtained only from the specific analyte of interest. In these embodiments, unbound analytes and unbound magnetic labels do not produce a detectable signal. As such, the real-time signal that is obtained is only from the specific magnetically-labeled analyte of interest bound to the magnetic sensor and substantially no signal is obtained from unbound magnetic labels or other reagents (e.g., analytes not specifically bound to the sensor).

In some embodiments, the signal is observed while the assay device is in a wet condition. By "wet" or "wet condition" is meant that the assay composition (e.g., an assay composition that includes a sample, a magnetic label, and a capture probe) is still in contact with the surface of the magnetic sensor. As such, there is no need to perform any washing steps to remove the non-binding moieties that are not of interest or the excess unbound magnetic labels or capture probes. In certain embodiments, the use of magnetic labels and magnetic sensors, as described above, facilitates "wet" detection because the signal induced in the magnetic sensor by the magnetic label decreases as the distance between the magnetic label and the surface of the magnetic sensor increases. For example, the use of magnetic labels and magnetic sensors, as described above, may facilitate "wet" detection because the magnetic field generated by the magnetic labels decreases as the distance between the magnetic label and the surface of the magnetic sensor increases. In some instances, the magnetic field of the magnetic label bound to the surface-bound analyte significantly exceeds the magnetic field from the unbound magnetic labels dispersed in solution. For example, as described above, a real-time analyte-specific signal may be obtained only from the specific magnetically-labeled analyte of interest bound to the magnetic sensor and substantially no signal may be obtained from unbound magnetic labels dispersed in solution (e.g., not specifically bound to the sensor). The unbound magnetic labels dispersed in solution may be at a greater distance from the surface of the magnetic sensor and may be in Brownian motion, which may reduce the ability of the unbound magnetic labels to induce a detectable change in the resistance of the magnetic sensor.

Assay Protocol

A typical assay protocol, as well as the individual components of the assay, is described in the following sections. In certain embodiments, the method includes contacting a magnetic sensor array with an assay composition that includes a sample. The magnetic sensor array may then be contacted with a magnetic label and a capture probe configured to bind to the magnetic label. A signal is obtained from the sensor to detect the presence of the analyte in the sample. Each of these steps will now be described in greater detail.

Sample

As described above, assay compositions that may be assayed in the subject methods include a sample. Samples that may be assayed in the subject methods may vary, and include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analytes of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure.

In certain embodiments, the samples of interest are biological samples, such as, but not limited to, urine, blood, serum, plasma, saliva, perspiration, feces, cheek swabs, cerebrospinal fluid, cell lysate samples, and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In some instances, the samples of interest are water, food or soil samples.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

Magnetic Labels

Assay compositions that may be assayed in the subject methods include a magnetic label. Magnetic labels are labeling moieties that are detectable by a sensor, such as a magnetic sensor, when the magnetic label is positioned near the sensor. While the distance between the magnetic label and sensor surface during detection may vary depending on the nature of the specific magnetic label and sensor surface, in some instances this distance ranges from 1 nm to 1000 nm from the surface of the sensor, or 1 nm to 800 nm from the surface of the sensor, such as from 5 nm to 500 nm, including from 5 nm to 100 nm. In certain embodiments, the magnetic labels are detectable labels that are configured to specifically bind to an analyte of interest. The terms "specific binding," "specifically bind," and the like, refer to the ability of a first binding molecule or moiety (e.g., a target-specific binding moiety) to preferentially bind directly to a second binding molecule or moiety (e.g., a target molecule) relative to other molecules or moieties in a solution or reaction mixture. In certain embodiments, the affinity between a first binding molecule or moiety and a second binding molecule or moiety when they are specifically bound to each other in a binding complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

Binding of the magnetic label to the analyte of interest allows the analyte of interest to be detected by a sensor, such as a magnetic sensor, when the analyte of interest, and thus the bound magnetic label, is positioned near the sensor. In some cases, the magnetic labels are configured to bind directly to an analyte of interest. In other cases, the magnetic labels are configured to indirectly bind to an analyte of interest. For instance, a magnetic label may be configured to specifically bind to a capture probe, and the capture probe may be configured to specifically bind to the analyte of interest. Thus, binding of the magnetic label and the analyte of interest to the capture probe indirectly binds the magnetic label to the analyte of interest, e.g., to produce a labeled analyte. In some instances, the binding of the magnetic label and analyte to the capture probe is simultaneous.

In certain embodiments, the magnetic label is functionalized with one member of a binding pair. By "binding pair" or "specific binding pair" is meant two complementary binding molecules or moieties that specifically bind to each other in a binding complex. For example, a magnetic label may be functionalized with a first member of a binding pair and an analyte of interest may be functionalized with a second member of a binding pair. Thus, contacting the first and second members of the binding pair may form a binding complex between the magnetic label and the analyte of interest. In other cases, a magnetic label is functionalized with a first member of a binding pair and a capture probe is functionalized with a second member of a binding pair. Thus, contacting the first and second members of the binding pair may form a binding complex between the magnetic label and the capture probe. As described above, in some cases, the capture probe is configured to specifically bind to an analyte of interest. As such, the magnetic label may be indirectly bound to the analyte of interest through the binding complex formed between the magnetic label and the capture probe. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the magnetic label is functionalized with streptavidin and the capture probe is functionalized with biotin. As such, the magnetic label may specifically bind to the capture probe through the specific binding interaction between streptavidin and biotin. Other types of binding interactions are also possible. For example, the magnetic label may be functionalized with biotin and the capture probe may be functionalized with streptavidin. Alternatively, the magnetic label and the capture probe may be functionalized with complementary members of other specific binding pairs, as described above.

In some instances, the magnetic label is stably associated with one member of a binding pair. By "stably associated" is meant that the magnetic label and the member of the binding pair maintain their position relative to each other in space under the conditions of use, e.g., under the assay conditions. As such, the magnetic label and the member of the binding pair can be non-covalently or covalently stably associated with each other. Examples of non-covalent association include non-specific adsorption, binding based on electrostatic (e.g., ion-ion pair interactions), hydrophobic interactions, hydrogen bonding interactions, and the like. Examples of covalent binding include covalent bonds formed between the member of the binding pair and a functional group present on the surface of the magnetic label.

In certain embodiments, the magnetic labels are colloidal. The terms "colloid" or "colloidal" refer to a mixture in which one substance is dispersed throughout another substance. Colloids include two phases, a dispersed phase and a continuous phase. In some instances, colloidal magnetic labels remain dispersed in solution and do not precipitate or settle out of solution. Colloidal magnetic labels that remain dispersed in solution may facilitate a minimization in background signals and non-specific interaction of the magnetic labels with the magnetic sensor. For example, the methods may include contacting a magnetic sensor with an assay composition that includes a sample and a magnetic label, such that an analyte of interest in the sample is bound to the surface of the magnetic sensor. Because the colloidal magnetic labels remain dispersed in solution, the magnetic labels are not positioned near enough to the magnetic sensor to induce a detectable signal in the magnetic sensor, which facilitates a minimization in background signals. In some cases, specific binding of the magnetic labels to the surface-bound analyte positions the magnetic label near the magnetic sensor, such that a detectable signal is induced in the magnetic sensor.

Magnetic labels that may be employed in various methods (e.g., as described herein) may vary, and include any type of label that induces a detectable signal in a magnetic sensor when the magnetic label is positioned near the surface of the magnetic sensor. For example, magnetic labels may include, but are not limited to, magnetic labels, optical labels (e.g., surface enhanced Raman scattering (SERS) labels), fluorescent labels, and the like. Each of these types of magnetic labels is discussed in more detail below.

Magnetic labels are labeling moieties that, when sufficiently associated with a magnetic sensor, are detectable by the magnetic sensor and cause the magnetic sensor to output a signal. For example, the presence of a magnetic label near the surface of a magnetic sensor may induce a detectable change in the magnetic sensor, such as, but not limited to, a change in resistance, conductance, inductance, impedance, etc. In some cases, the presence of a magnetic label near the surface of a magnetic sensor induces a detectable change in the resistance of the magnetic sensor. Magnetic labels of interest may be sufficiently associated with a magnetic sensor if the distance between the center of the magnetic label and the surface of the sensor is 1000 nm or less, such as 800 nm or less, such as 400 nm or less, including 100 nm or less.

In certain instances, the magnetic labels include one or more materials selected from paramagnetic, superparamagnetic, ferromagnetic, ferromagnetic, antiferromagnetic materials, combinations thereof, and the like. For example, the magnetic labels may include superparamagnetic materials. In certain embodiments, the magnetic labels are configured to be nonmagnetic in the absence of an external magnetic field. By "nonmagnetic" is meant that the magnetization of a magnetic labels is zero or averages to zero over a certain period of time. In some cases, the magnetic label may be nonmagnetic due to random flipping of the magnetization of the magnetic label over time. Magnetic labels that are configured to be nonmagnetic in the absence of an external magnetic field may facilitate the dispersion of the magnetic labels in solution because nonmagnetic labels do not normally agglomerate in the absence of an external magnetic field or even in the presence of a small magnetic field in which thermal energy is still dominant. In certain embodiments, the magnetic labels include superparamagnetic materials or synthetic antiferromagnetic materials. For instance, the magnetic labels may include two or more layers of antiferromagnetically-coupled ferromagnets.

In certain embodiments, the magnetic labels are high moment magnetic labels. The magnetic moment of a magnetic label is a measure of its tendency to align with an external magnetic field. By "high moment" is meant that the magnetic labels have a greater tendency to align with an external magnetic field. Magnetic labels with a high magnetic moment may facilitate the detection of the presence of the magnetic labels near the surface of the magnetic sensor because it is easier to induce the magnetization of the magnetic labels with an external magnetic field.

In certain embodiments, the magnetic labels include, but are not limited to, Co, Co alloys, ferrites, cobalt nitride, cobalt oxide, Co—Pd, Co—Pt, iron, iron oxides, iron alloys, Fe—Au, Fe—Cr, Fe—N, Fe$_3$O$_4$, Fe—Pd, Fe—Pt, Fe—Zr—Nb—B, Mn—N, Nd—Fe—B, Nd—Fe—B—Nb—Cu, Ni, Ni alloys, combinations thereof, and the like. Examples of high moment magnetic labels include, but are not limited to, Co, Fe or CoFe nanocrystals, which may be superparamagnetic at room temperature, and synthetic antiferromagnetic nanoparticles.

In some embodiments, the surface of the magnetic label is modified. In certain instances, the magnetic labels may be coated with a layer configured to facilitate stable association of the magnetic label with one member of a binding pair, as described above. For example, the magnetic label may be coated with a layer of gold, a layer of poly-L-lysine modified glass, dextran, and the like. In certain embodiments, the magnetic labels include one or more iron oxide cores imbedded in a dextran polymer. Additionally, the surface of the magnetic label may be modified with one or more surfactants. In some cases, the surfactants facilitate an increase in the water solubility of the magnetic labels. In certain embodiments, the surface of the magnetic labels is modified with a passivation layer. The passivation layer may facilitate the chemical stability of the magnetic labels in the assay conditions. For example, the magnetic labels may be coated with a passivation layer that includes gold, iron oxide, polymers (e.g., polymethylmethacrylate films), and the like.

In certain embodiments, the magnetic labels have a spherical shape. Alternatively, the magnetic labels can be disks, rods, coils, or fibers. In some cases, the size of the magnetic labels is such that the magnetic labels do not interfere with the binding interaction of interest. For example, the magnetic labels may be comparable to the size of the analyte and the capture probe, such that the magnetic labels do not interfere with the binding of the capture probe to the analyte. In some cases, the magnetic labels are magnetic nanoparticles, or contain multiple magnetic nanoparticles held together by a suitable binding agent. In some embodiments, the average diameter of the magnetic labels is from 5 nm to 250 nm, such as from 5 nm to 150 nm, including from 10 nm to 100 nm, for example from 25 nm to 75 nm. For example, magnetic labels having an average diameter of 5 nm, 10 nm, 20 nm, 25 nm, 30 nm, 35 nm, 40 nm, 45 nm, 50 nm, 55 nm, 60 nm, 70 nm, 80 nm, 90 nm, or 100 nm, as well as magnetic labels having average diameters in ranges between any two of these values, may be used with the subject methods. In some instances, the magnetic labels have an average diameter of 50 nm.

Magnetic labels and their conjugation to biomolecules are further described in U.S. Ser. No. 12/234,506, filed Sep. 19, 2008, and entitled "Analyte Detection with Magnetic Sensors", the disclosure of which is hereby incorporated by reference in its entirety.

Assay Composition Production

In some instances, the method includes producing the assay composition by sequentially contacting the magnetic sensor array (e.g., array of biosensors) with the sample and the magnetic label. For example, the method may include contacting the magnetic sensor array first with the sample and subsequently with the magnetic label. Alternatively, the method may include contacting the magnetic sensor array first with the magnetic label and subsequently with the sample.

In other embodiments, the method includes combining the sample and the magnetic label to produce the assay composition and then contacting the magnetic sensor array with the assay composition. For instance, the method may include first combining the sample and the magnetic label to produce the assay composition. Then the magnetic sensor may be contacted with the assay composition, as described above. Subsequently, the method may include contacting the magnetic sensor with the capture probe, as described in detail below.

Capture Probe

A capture probe can be any molecule that specifically binds to a protein or nucleic acid sequence that is being targeted (e.g., the analyte of interest). Depending on the nature of the analyte, capture probes can be, but are not limited to, (a) single strands of DNA complementary to a unique region of the target DNA or RNA sequence for the detection of nucleic acids; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; and the like.

In certain embodiments, the capture probe includes an antibody. The capture probe antibody may specifically bind to an analyte of interest. In some cases, the capture probe is a modified antibody. The modified antibody may be configured to specifically bind to the analyte of interest and may also include one or more additional members of a specific binding pair. The one or more members of a specific binding pair may be configured to specifically bind to a complementary member of the specific binding pair. In certain instances, the complementary member of the specific binding pair is bound to the magnetic label, as described above.

For example, the capture probe may be an antibody that specifically binds to an analyte of interest. In addition, the capture probe may be modified to include biotin. As described above, in certain embodiments, magnetic labels may be modified to include streptavidin. As such, the capture probe may be configured to specifically bind to the analyte of interest (e.g., through an antibody-antigen interaction) and to specifically bind to the magnetic label (e.g., through a streptavidin-biotin interaction). In some cases, the capture probe is configured to bind to the analyte of interest and the magnetic label. Stated another way, the capture probe may be configured such that specific binding of the analyte to the capture probe does not significantly interfere with the ability of the capture probe to specifically bind to the magnetic label. Similarly, the capture probe may be configured such that specific binding of the magnetic label to the capture probe does not significantly interfere with the ability of the capture probe to specifically bind to the analyte.

In certain embodiments, the capture probe specifically binds to an analyte of interest. In some cases, the capture probe can be identified so that the presence of the analyte of interest can then be detected. Capture probes may be identified by any of the methods described herein. For example, as described above, analytes may be directly or indirectly bound to a magnetic sensor. The capture probe may contact and specifically bind to the analyte of interest. As indicated above, the capture probe may be configured to bind to a magnetic label and the analyte of interest. In certain instances, simultaneous binding of the capture probe to surface-bound analyte and the magnetic label positions the magnetic label within the detection range of the magnetic sensor, such that a detectable signal is induced in the magnetic sensor.

In some cases, false-positive signals due to non-specific binding of the capture probe to moieties not of interest are minimized. For example, non-specific binding of the capture probe to other moieties not of interest, which are not bound to the surface of the magnetic sensor and remain in solution, will not induce a detectable or non-negligible signal in the magnetic sensor because the magnetic label bound to the capture probe will not be positioned within the detection range of the magnetic sensor.

As described above, the magnetic label may be colloidal, such that the magnetic label remains dispersed in the assay composition solution. In certain instances, the kinetics of the capture probe diffusion to the surface of the magnetic sensor and binding to the analyte is significantly faster than the kinetics of the diffusion of the magnetic labels to the surface of the magnetic sensor. Having faster kinetics for the binding of the capture probe to the analyte than the diffusion of the magnetic label to the surface of the magnetic sensor may facilitate a minimization in false positive signals due to non-specific positioning of the magnetic label within the detection range of the magnetic sensor.

In certain embodiments, the magnetic sensor arrays are contacted with the capture probe after the magnetic sensor arrays are contacted with the assay composition. Thus, the methods may include first producing an assay composition that includes a sample and a magnetic label (e.g., in a first set of fluid reservoirs on a reservoir plate). The magnetic sensor array may then be contacted with the assay composition. Subsequently, the magnetic sensor array may be contacted with a capture probe.

Other methods are also possible. For example, the method may include first contacting the magnetic sensor arrays to the capture probe, and subsequently contacting the magnetic sensor arrays to the assay composition, where the assay composition includes a sample and a magnetic label. In both of the methods described above, the magnetic label is present in the assay composition prior to contacting the magnetic sensor array to the capture probe.

As described above, in some instances, the methods are wash-free methods of evaluating the presence of one or more analytes in a sample. As such, in certain embodiments, contacting the magnetic sensor arrays with assay components does not include any washing steps before or after contacting the magnetic sensor arrays with each component of the assay composition. Thus, no washing step is performed either before or after the magnetic sensor is contacted with any of the assay components.

Obtaining a Signal to Determine Whether an Analyte is Present in a Sample

Embodiments of the subject methods also include obtaining a signal from a magnetic sensor to detect the presence of an analyte in a sample. As described above, a magnetic label may be bound, either directly or indirectly, to the analyte, which in turn may be bound, either directly or indirectly, to the magnetic sensor. If the bound magnetic label is positioned within the detection range of the magnetic sensor, then the magnetic sensor may provide a signal indicating the presence of the bound magnetic label, and thus indicating the presence of the analyte.

Magnetic sensors may be configured to generate an electrical signal in response to a magnetic label in proximity to a surface of the magnetic sensor. For example, a change in the resistance of the magnetic sensor may be induced by changes in the local magnetic field. In some cases, binding of a magnetic label (e.g., a magnetic label) in close proximity to the magnetic sensor induces a detectable change in the local magnetic field of the magnetic sensor. For example, the magnetic field created by the magnetic labels that are bound to the analytes of interest may exceed the magnetic field that is created by unbound magnetic labels that remain dispersed in the sample. Changes in the local magnetic filed of the magnetic sensor may be detected as a change in the resistance of the magnetic sensor. In certain embodiments, unbound magnetic labels do not produce a detectable signal in the magnetic sensor.

Utility

The subject systems and methods find use in a variety of different applications where determination of the presence or absence, and/or quantification of one or more analytes in a sample is desired. The subject systems and methods also find use in applications where the screening of a plurality of samples is desired. In certain embodiments, the methods are directed to detection of a set of biomarkers, e.g., two or more distinct protein biomarkers, in a plurality of samples. For example, the methods may be used in the rapid detection of two or more disease biomarkers in a group of serum samples, e.g., as may be employed in the diagnosis of a disease condition in a subject, in the ongoing management or treatment of a disease condition in a subject, etc.

In certain embodiments, the subject systems and methods find use in detecting biomarkers. In some cases, the subject systems and methods may be used to detect the presence or absence of particular biomarkers, as well as an increase or decrease in the concentration of particular biomarkers in blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject methods and systems. Furthermore, the early detection of biomarkers associated with diseases is facilitated by the picomolar and/or femtomolar sensitivity of the subject methods and systems. Due to the capability of detecting multiple biomarkers on a single magnetic sensor device, the presently disclosed assay systems and methods finds use in screening of a plurality of samples in multiplexed molecular diagnostics.

In certain embodiments, the subject systems and methods find use in detecting biomarkers for a disease or disease state. In some cases, the disease is a cellular proliferative disease, such as but not limited to, a cancer, a tumor, a papilloma, a sarcoma, or a carcinoma, and the like. Thus, the subject systems and methods find use in detecting the presence of a disease, such as a cellular proliferative disease, such as a cancer, tumor, papilloma, sarcoma, carcinoma, or the like. In certain embodiments, the subject systems and methods find use in detecting biomarkers for an infectious disease or disease state. In some cases, the biomarkers can be molecular biomarkers, such as but not limited to proteins, nucleic acids, carbohydrates, small molecules, and the like. Similarly, the subject methods, systems and kits can be used to detect cardiovascular diseases, central nervous diseases, kidney failures, diabetes, autoimmune diseases, and many other diseases.

In certain embodiments, the subject methods, systems and kits can be used to detect the presence or absence, and/or quantification of one or more analytes in a plurality of samples for food and/or environmental safety. For example, the subject systems and methods can be used to determine the presence of analytes in a plurality of samples of potentially contaminated water, soil or food, such as for the detection of infectious disease agents, e.g., bacteria, viruses, molds, etc., including potential biological warfare agents.

Computer Related Embodiments

A variety of computer-related embodiments are also provided. Specifically, the data analysis methods described in the previous sections may be performed using a computer. Accordingly, provided is a computer-based system for analyzing data produced using the above methods in order to provide qualitative and/or quantitative determination of a binding interaction of interest.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, DVD-ROM, BD-ROM, a hard disk drive, a ROM or integrated circuit, a magneto-optical disk, a solid-state memory device, a computer readable card such as a PCMCIA card, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media does not include electronic signals in transit via a wireless protocol.

In certain embodiments, computer programming may include instructions for directing a computer to perform one or more assay steps to determine the presence of an analyte of interest in a sample. For example, the computer programming may include instructions for directing a computer to determine whether an analyte is present in a sample, e.g., determining the presence or absence of one or more analytes in a sample. In certain embodiments, the computer programming includes instructions for directing a computer to determine the presence of one or more analytes in the sample qualitatively and/or quantitatively. As described above, qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In some embodiments, the computer programming includes instructions for directing a computer to perform a uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the computer programming includes instructions for directing a computer to perform a uniplex analysis of the sample to determine the presence of the analyte of interest in the sample mixture.

In certain embodiments, the computer programming includes instructions for directing a computer to perform a multiplex analysis of two or more analytes in a sample. By "multiplex analysis" is meant that the presence of two or more distinct analytes, in which the two or more analytes are different from each other, is determined. For example, analytes may include detectable differences in their molecular structure, sequence, and the like, as described above. In some instances, the number of analytes is greater than 2, such as 4 or more, 6 or more, 8 or more, etc., up to 20 or more, e.g., 50 or more, including 100 or more, or 1000 or more distinct analytes. In certain embodiments, the computer programming includes instructions for directing a computer to perform a multiplex analysis of 2 to 1000 distinct analytes, such as 4 to 500 distinct analytes, including 4 to 200 distinct analytes, or 4 to 100 distinct analytes, or 4 to 50 distinct analytes, or 4 to 20 distinct analytes. In certain embodiments, the computer programming includes instructions for directing a computer to perform several multiplex assays in parallel substantially simultaneously.

With respect to computer readable media, "permanent memory" refers to memory that is permanent. Permanent memory is not erased by termination of the electrical supply to a computer or processor. Computer hard-drive, CD-ROM, DVD-ROM, BD-ROM, and floppy disk are all examples of permanent memory. Random Access Memory (RAM) is an example of non-permanent memory. A file in permanent memory may be editable and re-writable.

Kits

Also provided are kits for practicing one or more embodiments of the above-described methods. The subject kits may vary, and may include various devices and reagents. Reagents and devices include those mentioned herein with respect to magnetic sensor devices or components thereof (such as a magnetic sensor array), magnetic labels, capture probes, analyte-specific probes, buffers, etc. The reagents, magnetic labels, capture probes, etc. may be provided in separate containers, such that the reagents, magnetic labels, capture probes, etc. may be used individually as desired. Alternatively, one or more reagents, magnetic labels, capture probes, etc. may be provided in the same container such that the one or more reagents, magnetic labels, capture probes, etc. is provided to a user pre-combined.

In certain embodiments, the kits include a magnetic sensor device as described above, and a magnetic label. For example, the magnetic label may be a magnetic nanoparticle, as described above.

In some instances, the kits include at least reagents finding use in the methods (e.g., as described above); and a computer readable medium having a computer program stored thereon, wherein the computer program, when loaded into a computer, operates the computer to qualitatively and/or quantitatively determine a binding interaction of interest from a real-time signal obtained from a magnetic sensor; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Bluray, computer readable memory device (e.g., a flash memory drive), etc., on which the information has been recorded. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Introduction

Capture probes on the magnetic sensor surface of a magnetic sensor array specifically bound to target proteins in a patient sample. Detection antibodies bound to the "captured" proteins, forming a so called sandwich structure with target protein and capture probes. Finally, magnetic nanotags labeled the detection antibodies while an external magnetic field was applied to the sensor and the magnetic field produced by the nanotags was measured electrically by a computer to determine the original concentration of target protein present in the sample.

The same sensor array can be adapted to detect a variety of different molecular targets by modifying the capture probe molecules and the surface chemistry, which allows the sensor array to be used for multiplex analyte detection assays. An individual magnetic sensor site-specifically detects the presence of the magnetic nanotag by the generated magnetic field, using a magnetic sensor, such as a magnetic tunnel junction (MTJ, alternatively referred to as a tunnel magneto resistance, TMR) sensor. In some instances, MTJs have a magnetoresistance (MR) ratio that is one order of magnitude or more larger than that of a spin valve sensor.

For example, giant magnetoresistive (GMR) spin valve sensors have a maximum relative resistance change of ~12%, while embodiments of the subject MTJ sensor may have a maximum relative resistance change of >100% (see FIG. 1). MTJ sensors can have >10× more magnetoresistance (resistance change in response to magnetic fields) than spin valve sensors. Due to the signal scaling behavior observed in the subject assay system, where each order of magnitude increase in analyte concentration results in approximately doubling of the magnetic signal, the assay resolution may be increased by greater than 10× as compared to spin valve sensors. Since the magnetic signal scales roughly as Signal=$2^{Log\,[c]}$, where c is the analyte concentration, a 10× larger magnetic signal may result in roughly 3 orders of magnitude better assay resolution. In other words, the lower limit of quantitation (LLOQ) of the assay platform may be reduced by about 3 orders of magnitude.

Summary

The biologically active sensor area for protein or DNA detection, about 140 µm by 140 µm, was significantly larger than the individual magnetic labels (see FIGS. 2(a) and 2(b)). Since the area of an individual MTJ sensor was generally smaller (to minimize pinhole or other defects), the 140 µm by 140 µm sensor area included a series connection of MTJ sensors (labeled as tunnel magneto resistance, TMR sensors), as shown in FIG. 2(a). The current passed vertically through several MTJ sensors, which was accomplished by connecting the MTJ sensors in series, alternatingly sandwiched between a top lead (electrode) layer and a bottom lead (electrode) layer. The sense current flowed through the MTJ sensors in series and in Current Perpendicular to Plane (CPP) mode. The spin valve sensors can be made of long stripes connected end-to-end using one lead layer, as shown in FIG. 2(b).

Top lead and bottom lead geometry with respect to the MTJ sensor was designed such that shorting defects were minimized. In addition, the size and pitch of the MTJ sensors was designed such that the entire sensor array was patterned by ion milling without excessive over-etching or re-deposition.

Magnetic Sensor Design

Figure 3:
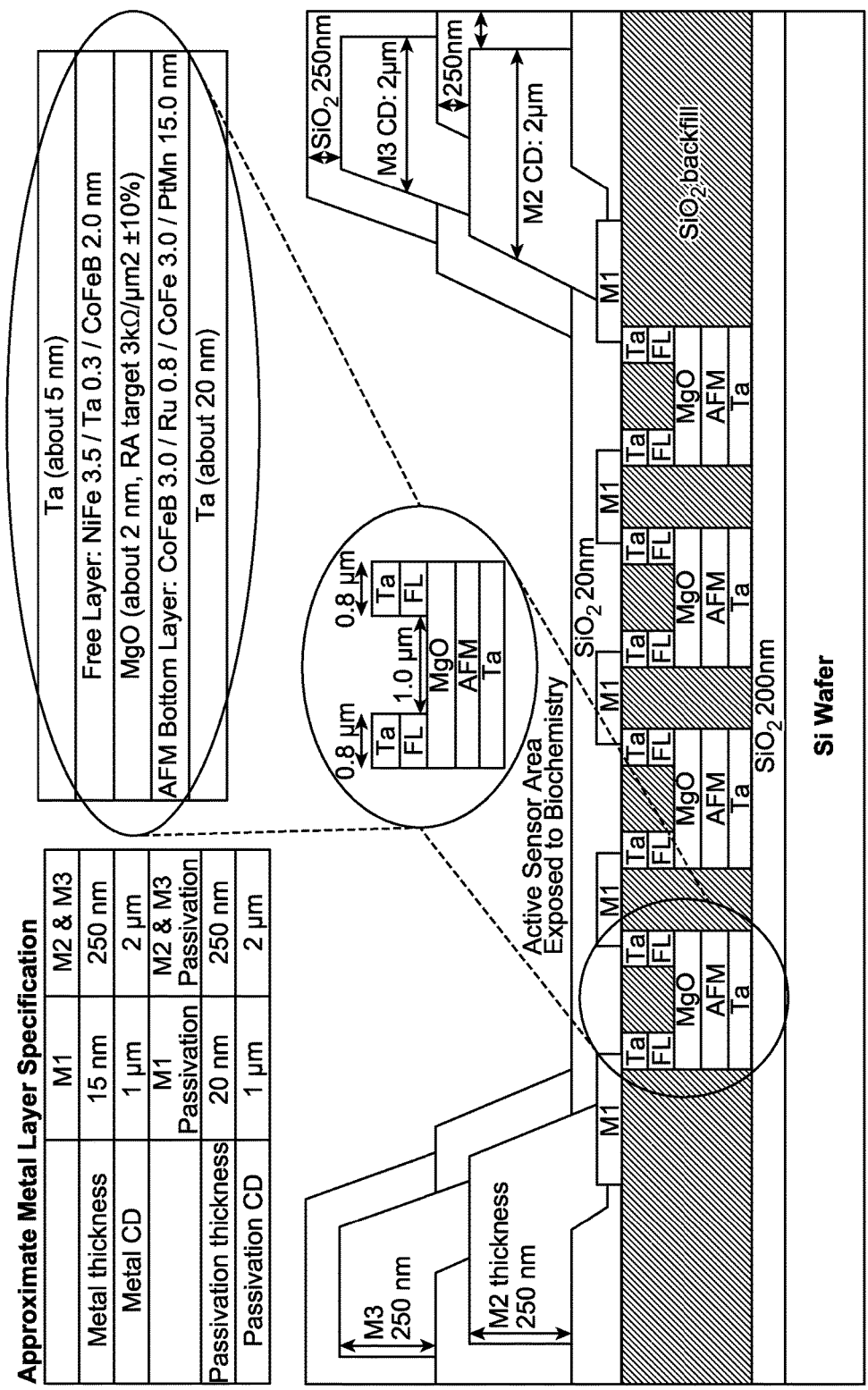
FIG. 3 shows a schematic (not actual proportions) cross-section of a magnetic sensor device that includes an array of MTJ sensors which together form a single biosensor, according to embodiments of the present disclosure.

A cross-section an MTJ biosensor is shown in FIG. 3. A support of Si(100) with 2000 angstroms (200 nm) of thermal oxide, and MTJ sensor that included layers of Ta200/PtMn150/CoFe30/Ru8/CoFeB30/MgO16/CoFeB15/Ta3/NiFe15/Ru100 (all thickness in angstrom) was used. The MR ratio was >100%, and the resistance-junction area (RA) product was RA=2-4 kOhm. The MTJ sensor was etched according to the design in FIG. 2(a). The thickness and critical dimension (CD) of the metal layers (M1, M2 & M3) are listed in the table insert in FIG. 3.

The thicknesses of metal layer M1 and its overlying passivation layer was minimized without compromising chemical integrity or electrical integrity of the MTJ sensor in the presence of biological fluids. The 20 nm thick $SiO_2$ passivation layer insulated the MTJ sensor from the corrosive effects associated with the chemistry of the biological assay process while the top lead (electrode) connected adjacent MTJ sensors with minimum addition to electrical resistance in the MTJ circuit.

Minimizing the distance between the specifically bound magnetic labels and the MTJ sensors facilitated achieving high sensitivity. As shown in FIG. 3 and FIG. 2(a), the magnetic separation distance, i.e., the distance between the free layer in the MTJ sensor and the bottom of the magnetic particle, depended three film layers: the MTJ cap thickness, the top lead (electrode) thickness, and the passivation layer thickness. The thicknesses given in FIG. 3 for these layers was typical, but can be changed by −50% to +300%.

Figure 4:
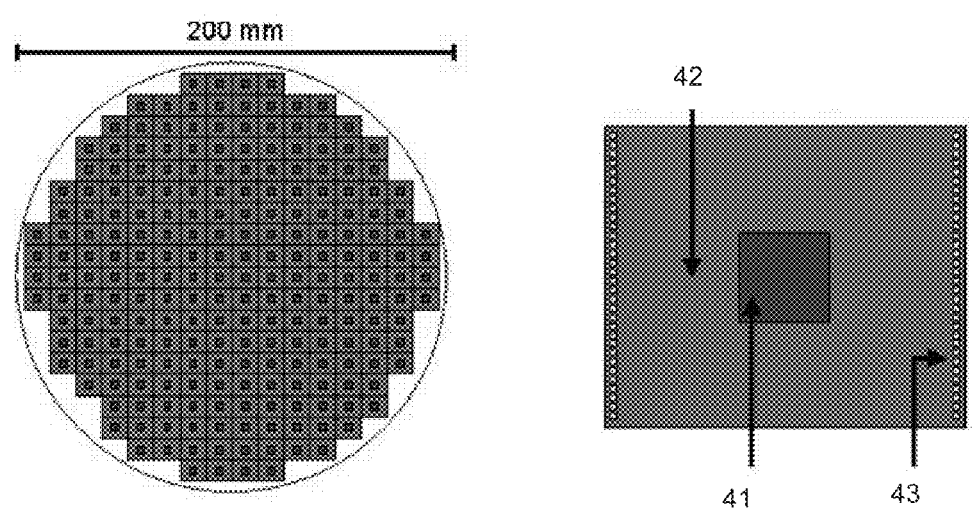
FIG. 4 shows wafer (left) and chip, e.g., magnetic sensor device (right), schematics of MTJ biosensors, according to embodiments of the present disclosure.

As shown in FIG. 4, a biosensor array (41) included 32 MTJ sensors, had dimensions of 3 mm×3 mm and an area of 9 $mm^2$. The sensor array was provided within a 12 mm×10 mm sensor array chip area (42) of 120 $mm^2$. The sensor array also included 32 electrical connection points (43) arranged in a column on the right side of the array area. During production, this sensor array chip area yielded a total of 236 devices on a 200 mm wafer (FIG. 4, left). In certain embodiments, the sensor array chip area may be reduced to 6 mm×5 mm area of 30 $mm^2$, which can provide a total of 800 devices from a 200 mm wafer. Further reduction of chip area is possible to increase the device number per wafer which translates directly into cost reductions. In certain embodiments, a 150 mm diameter wafer may be used, which can provide between 100 to 1000 sensor array chips, depending on the size and number of sensors per chip.

Figure 5:
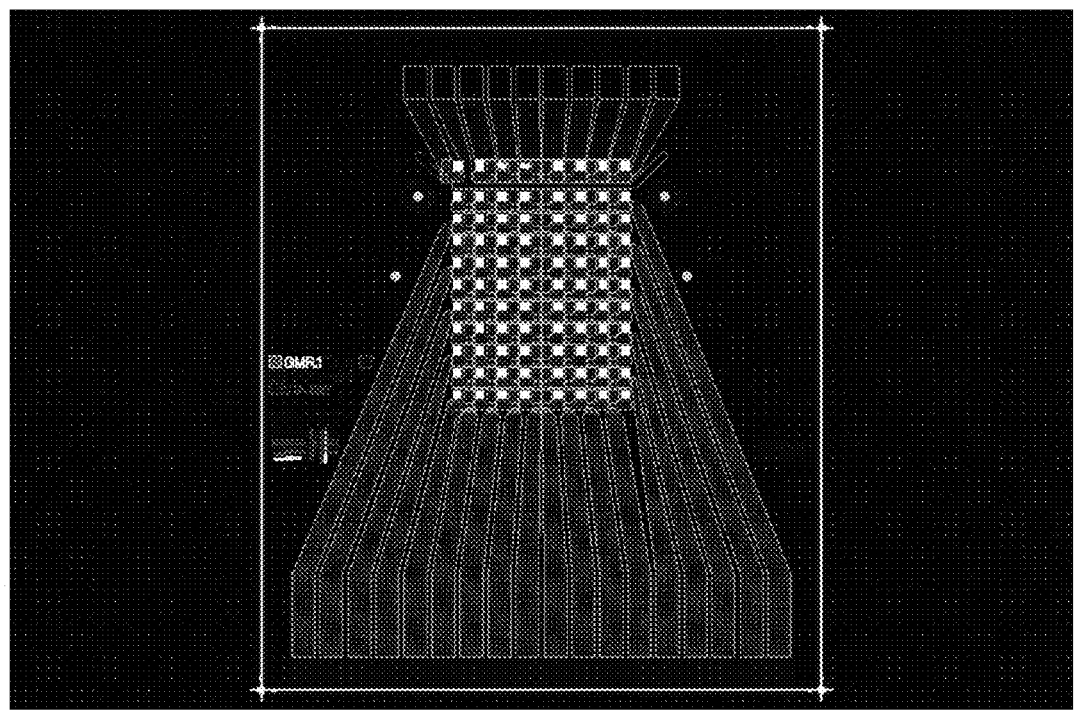
FIG. 5 shows a schematic of a MTJ biochip layout with 80 active biosensors, according to embodiments of the present disclosure.
Figure 8:
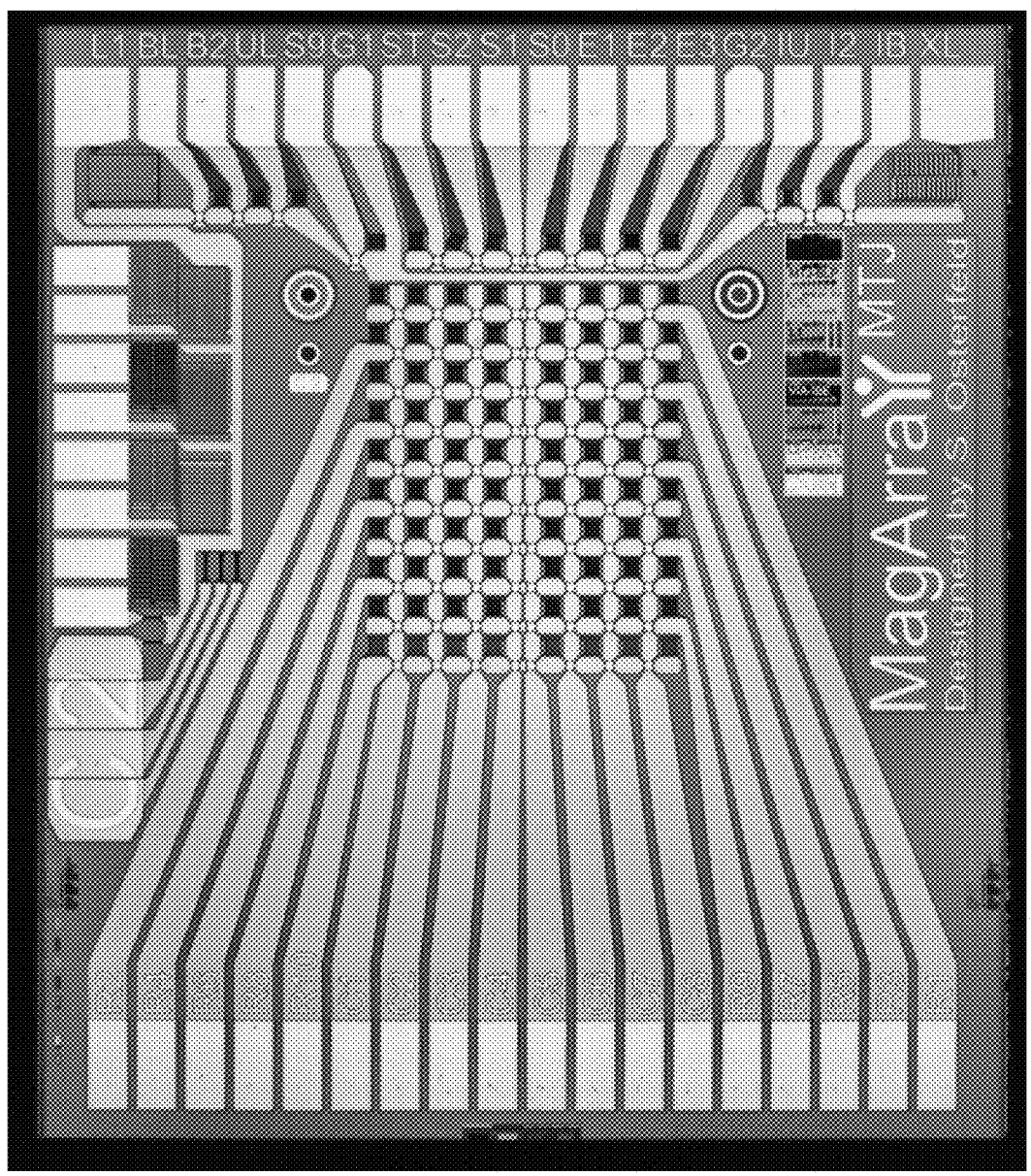
FIG. 8 shows an image of a 10 mm×12 mm biochip that includes an array of 80 MTJ biosensors, according to embodiments of the present disclosure.

FIG. 5 shows a schematic of a MTJ biochip layout with 80 active biosensors. FIG. 8 shows an image of a 10 mm×12 mm biochip that included an array of 80 MTJ sensors.

Using the MTJ sensor described in FIG. 3, 72 different MTJ biosensors were designed and fabricated, which were distinguished by variations in shape, size, and layer-to-layer overlap characteristics, such as the arrangement of sandwiching the MTJ sensor between the top and bottom leads (electrodes). In typical MTJ designs, the leads between which an MTJ sensor is be sandwiched are designed to extend beyond the MTJ sensor in every direction, as shown in the bottom left of FIG. 6, e.g., MTJ sensor designs 1 through 36. This typical design increased the risk of lead-to-lead shorting in those areas where the leads overlapped, but where no MTJ material was present.

Figure 6:
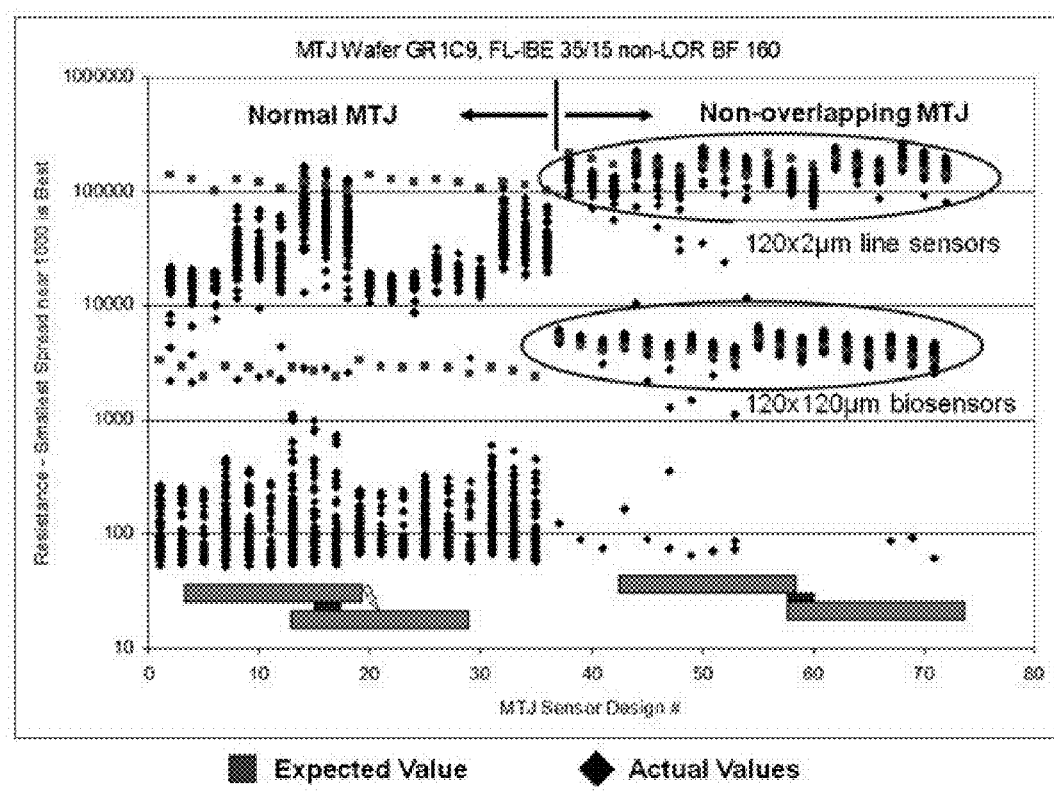
FIG. 6 shows a graph of experimental results of MTJ biosensors, according to embodiments of the present disclosure.

To reduce the risk of lead-to-lead shorting in MTJ biosensors, the subject MTJ sensor design had non-overlapping leads. The resulting MTJ sensor design is shown in FIG. 6, e.g., sensor designs 37 through 72. Here, the top leads only partially covered the MTJ sensor, and the bottom leads aligned with the edge of the MTJ sensor, as shown in the bottom right of FIG. 6.

In FIG. 6, the squares denote the expected resistance of functional MTJ sensors, according to how they were designed. The vertical lines show the distribution of actual resistances obtained for a sensor of a given design. Sensor designs where the experimentally obtained resistances (diamond data points) were grouped more closely around their expected resistance values (squares) were considered to be more suitable.

As shown in FIG. 6, the distribution of experimentally measured resistances from the "non-overlapping" sensor designs #37 thorough 72 were significantly closer to their expected resistance values. In contrast, the typical sensor designs 1 through 36 showed significant differences between the expected and actual values, which indicated a significant amount of lead-to-lead shorting. The significant reduction and/or elimination of lead-to-lead shorting resulted in greater accuracy of the subject non-overlapping sensor design.

Figure 7:
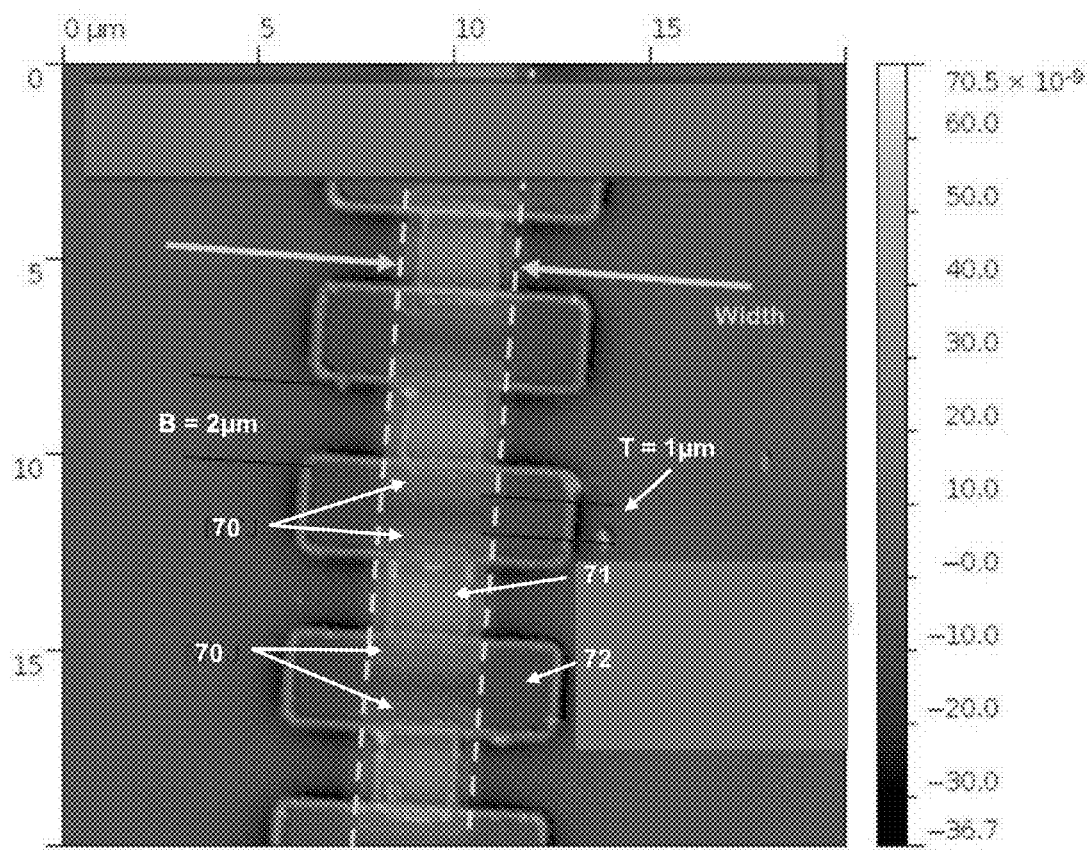
FIG. 7 shows a scanning electron micrograph image of an array of MTJ sensor elements with the MTJ sensor elements arranged in series, according to embodiments of the present disclosure.

FIG. 7 shows an image of a 2.6 µm width line-style sensor based on the non-overlapping MTJ sensor design described herein. The distance between adjacent top electrodes (T) was 1 µm, and the distance between adjacent bottom electrodes (B) was 2 µm. MTJ sensors (70) were arranged in series and located between opposing top electrodes (71) and bottom electrodes (72). The image was obtained in a scanning electron microscope. The sensor geometry resulted in a MR ratio of 190%.

A similarly designed biosensor had a width of 140 µm, which facilitated a maximization in the biological active sensor area. The 140 µm wide MTJ sensor had a MR ratio of 175%.

Example 2

Figure 9:
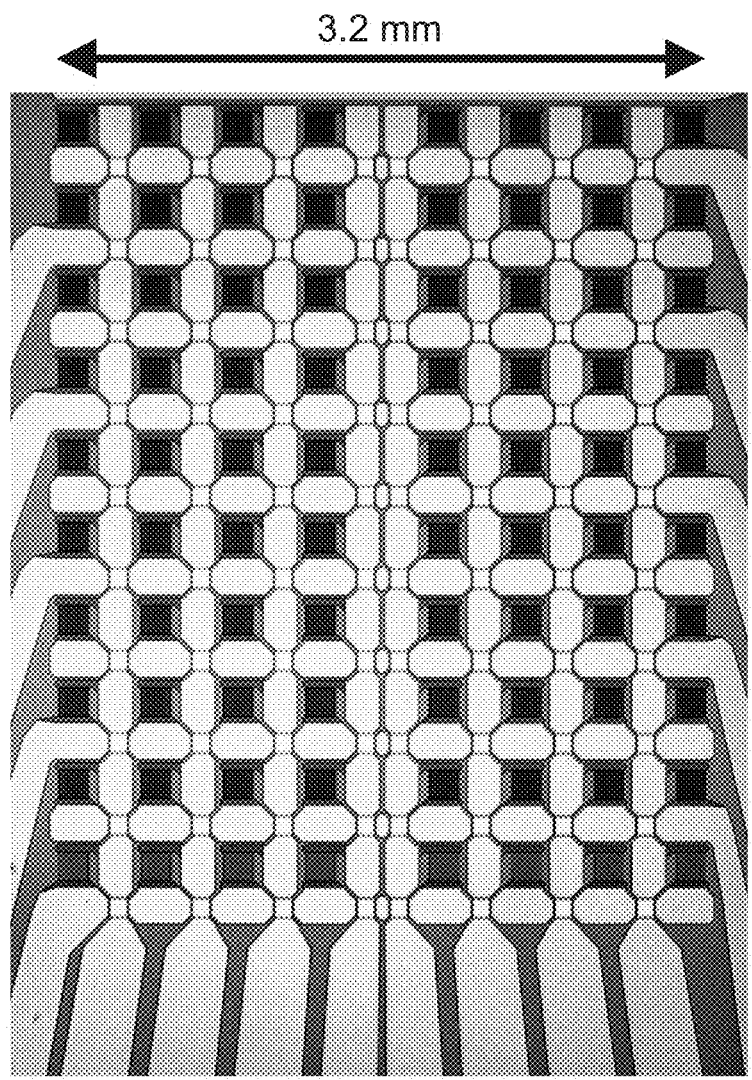
FIG. 9 shows an enlarged image of an array of 80 MTJ biosensors, according to embodiments of the present disclosure.
Figure 10:
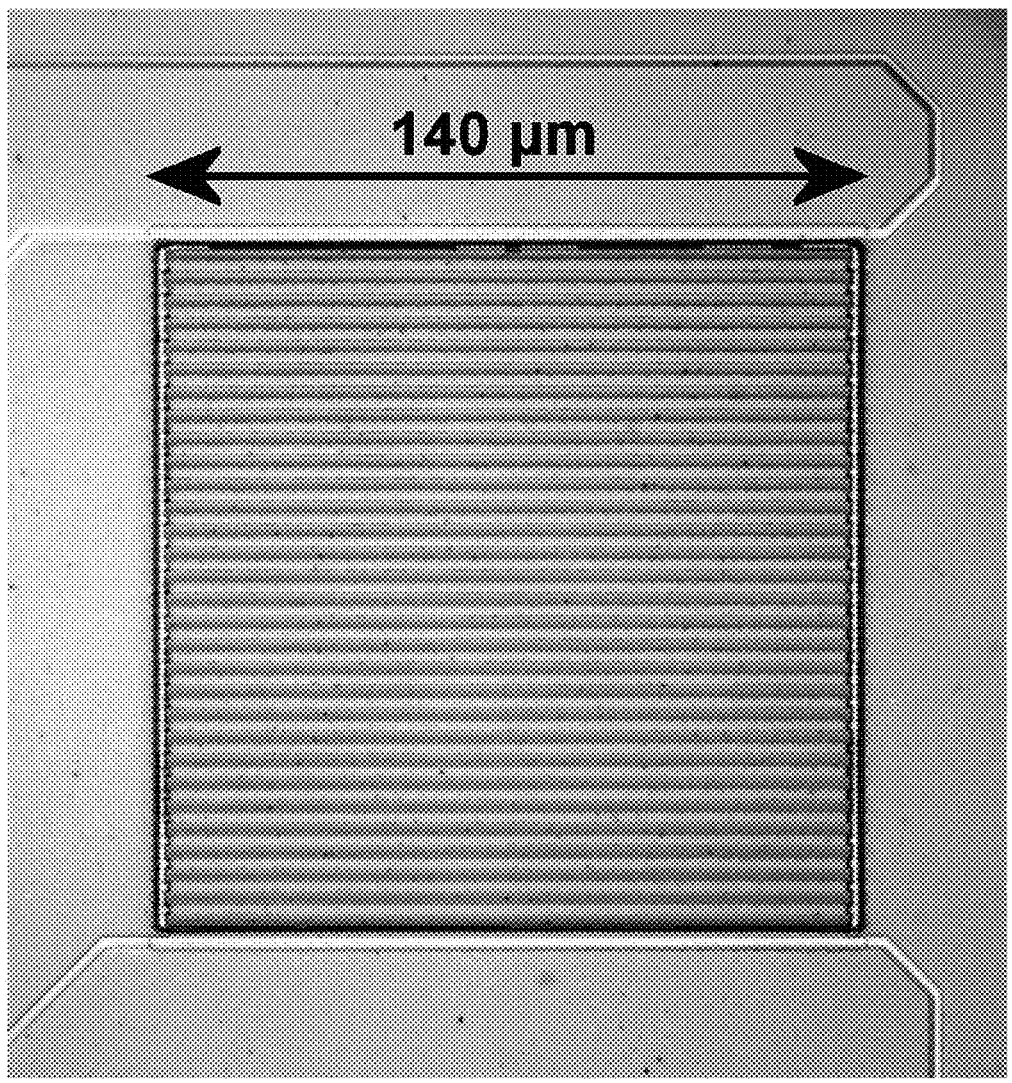
FIG. 10 shows an enlarged image of an individual MTJ biosensor, according to embodiments of the present disclosure.

Experiments were performed using a MTJ sensor array as described in Example 1, which contained an array of 80 MTJ sensors, to detect streptavidin-biotin binding in phosphate buffered saline (PBS) buffer. FIG. 9 shows an enlarged image of an array of 80 MTJ sensors. The array had dimensions of about 3.2 mm×3.8 mm. FIG. 10 shows an enlarged image of an individual MTJ sensor of the array prior to application of biotinylated bovine serum albumin (BSA) as described below. The sensor had dimensions of 140 µm×140 µm.

1. Chip Surface Preparation

The assembled chips were thoroughly washed with acetone, methanol, isopropanol, and de-ionized water. A 5-min UV ozone treatment (UVO Cleaner Model 42, Jelight) was used to remove organic residues. To form the base layer of the biofunctionalization, a 2% solution of polyethyleneimine (PEI, CAS 9002-98-6, Sigma-Aldrich) in deionized water was applied to the chip surface for 2 min. The chips were rinsed with deionized water and baked at 150° C. for 30 min to solidify the adsorbed PEI. Chip surface preparation as described above facilitated the adsorption of the capture protein, which was spotted on each sensor individually. The surface preparation could be performed by other methods which will result in a high density of exposed amine groups (—NH) at the chip surface.

2. Initial Protein Coating onto the Chip

Active sensors: Biotinylated BSA was diluted in 1×PBS buffer to a concentration of 40 sensors of the array were spotted with 1 nanoliter each of this solution. Within 60 seconds, each spot of solution dried out in a circular spot of sufficient size to cover the 140 µm×140 µm sensor.

Reference sensors: BSA was diluted in 1×PBS buffer to a concentration of 0.5% by weight. 40 sensors of the array were spotted with 1 nanoliter each of this solution. Within 60 seconds, each spot of solution dried out in a circular spot of sufficient size to cover the 140 µm×140 µm sensor.

3. Blocking of the Remaining Chip Surface

The chip was immersed in a solution of 5% by weight of BSA in 1×PBS buffer for 1 h to reduce nonspecific surface binding.

4. Rinsing of the Prepared Chip Surface

The chip was rinsed three times with rinsing buffer (0.1% BSA and 0.05% Tween 20 in 1×PBS)

5. Application of Magnetic Nanoparticles

The data recording was started, and after two minutes, 100 µL of streptavidin-coated magnetic nanoparticle solution (MACS 130-048-102, Miltenyi Biotec) was added to the chip.

Figure 11:
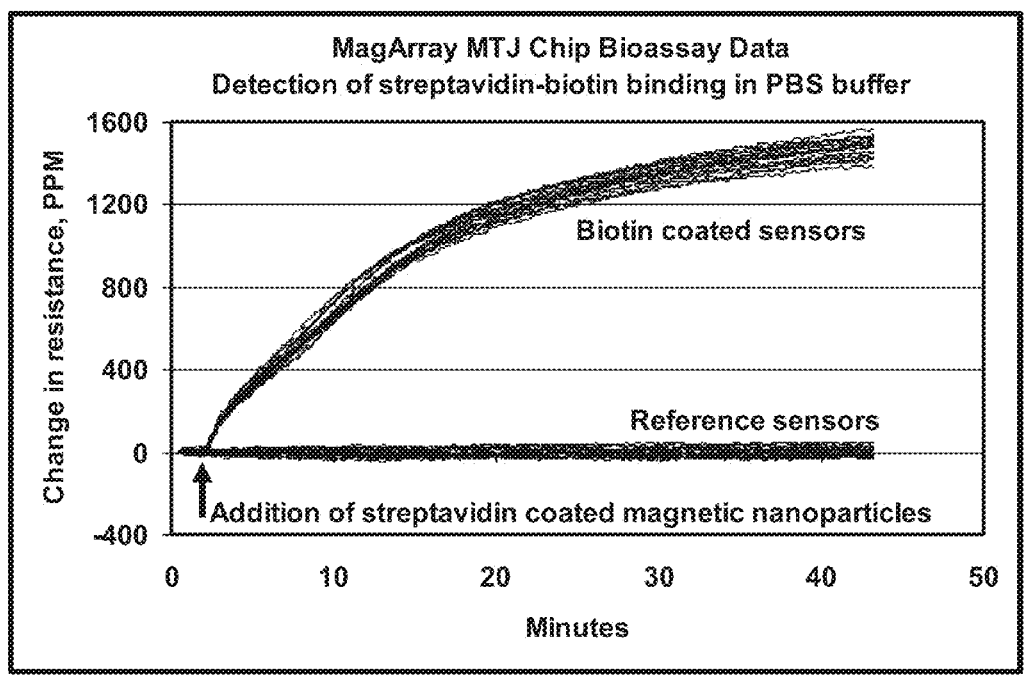
FIG. 11 shows a graph of the change in resistance (ppm) vs. time (min) for the detection of streptavidin-biotin binding in PBS buffer for biotin coated sensors as compared to reference sensors, according to embodiments of the present disclosure.

FIG. 11 shows a graph of the change in resistance (ppm) vs. time (min) for the detection of streptavidin-biotin binding in PBS buffer as described above. The graph shows the change in resistance for the biotin coated sensors as compared to reference sensors.

Although the foregoing embodiments has been described in some detail by way of illustration and example for purposes of clarity of understanding, it is readily apparent to those of ordinary skill in the art in light of the teachings of this present disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of the subject embodiments and are included within its spirit and scope. Furthermore, all examples and conditional language recited herein are principally intended to aid the reader in understanding the principles of embodiments of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed:

1. A magnetic sensor device comprising:
   a magnetic sensor comprising:
      two or more magnetic tunnel junction (MTJ) magnetoresistive elements electrically connected to each other in series;
      a first electrode contacting at least a portion of a surface of a first MTJ magnetoresistive element and extending beyond an edge of the surface of the first MTJ magnetoresistive element;
      a second electrode comprising a first end contacting at least a portion of an opposing surface of the first MTJ magnetoresistive element and a second end extending beyond an edge of the opposing surface of the first MTJ magnetoresistive element and contacting at least a portion of a surface of a second MTJ magnetoresistive element; and
an analyte-specific probe bound to a surface of the magnetic sensor,
wherein:
facing surfaces of the first and second electrodes are only overlapping where they contact the surface and the opposing surface of the MTJ magnetoresistive elements,
the first MTJ magnetoresistive element comprises a first free layer, the second MTJ magnetoresistive element comprises a second free layer, and the first and second MTJ magnetoresistive elements comprise a common antiferromagnetic layer and a common insulating layer between the antiferromagnetic layer and the first and second free layers, and
the magnetic sensor is configured to detect a magnetically-labeled analyte in a sample, wherein at least one of the first and second electrodes contacts less than an entire surface of one or more of the first and second MTJ magnetoresistive elements.

2. The magnetic sensor device of claim 1, wherein the first electrode contacts substantially the entire surface of the first MTJ magnetoresistive element.

3. The magnetic sensor device of claim 1, wherein the second electrode contacts substantially the entire opposing surface of the first MTJ magnetoresistive element.

4. The magnetic sensor device of claim 1, wherein an edge of the second electrode is aligned with the edge of the opposing surface of the first MTJ magnetoresistive element.

5. The magnetic sensor device of claim 1, further comprising a passivation layer disposed on the first electrode.

6. The magnetic sensor device of claim 1, comprising a magnetic sensor array comprising two or more of the magnetic sensors.

7. The magnetic sensor device of claim 6, wherein the magnetic sensor array comprises two or more distinct magnetic sensors each configured to specifically detect the same analyte.

8. The magnetic sensor device of claim 6, wherein the magnetic sensor array comprises two or more distinct magnetic sensors each configured to specifically detect a different analyte.

9. A kit comprising:
a magnetic sensor device of claim 1; and
a magnetic label.

10. The magnetic sensor device of claim 1, wherein the first and second electrodes extend from their respective edges of the first MTJ magnetoresistive element in different directions.

11. The magnetic sensor device of claim 1, wherein the first electrode contacts less than the entire surface of the first MTJ magnetoresistive element.

12. The magnetic sensor device of claim 1, wherein the antiferromagnetic layer comprises a first ferromagnetic layer, a metallic layer, a second ferromagnetic layer, and an antiferromagnetic layer.

13. The magnetic sensor device of claim 1, wherein the magnetic sensor array consists of two or more distinct magnetic sensors.

14. The magnetic sensor device of claim 1, wherein the first and second MTJ magnetoresistive elements are configured such that the distance between an associated magnetic label and the top surface of the first and second free layers of the MTJ magnetoresistive elements is from 5 nm to 1000 nm.

15. A magnetic sensor system comprising:
a magnetic sensor device comprising:
a magnetic sensor array comprising two or more magnetic sensors each comprising:
two or more magnetic tunnel junction (MTJ) magnetoresistive elements electrically connected to each other in series;
a first electrode contacting at least a portion of a surface of a first MTJ magnetoresistive element and extending beyond an edge of the surface of the first MTJ magnetoresistive element;
a second electrode comprising a first end contacting at least a portion of an opposing surface of the first MTJ magnetoresistive element and a second end extending beyond an edge of the opposing surface of the first MTJ magnetoresistive element and contacting at least a portion of a surface of a second MTJ magnetoresistive element; and
an analyte-specific probe bound to a surface of one or more magnetic sensors,
wherein:
facing surfaces of the first and second electrodes are only overlapping where they contact the surface and the opposing surface of the MTJ magnetoresistive elements,
the first MTJ magnetoresistive element comprises a first free layer, the second MTJ magnetoresistive element comprises a second free layer, and the first and second MTJ magnetoresistive elements comprise a common antiferromagnetic layer and a common insulating layer between the antiferromagnetic layer and the first and second free layers, and
the magnetic sensors are configured to detect a magnetically-labeled analyte in a sample; and
a magnetic field source, wherein at least one of the first and second electrodes contacts less than an entire surface of one or more of the first and second MTJ magnetoresistive elements.

16. The magnetic sensor system of claim 15, further comprising a processor configured to obtain an analyte-specific signal from the magnetic sensor device.

17. The magnetic sensor system of claim 15, wherein the magnetic sensor array is a two-dimensional array of magnetic sensors.

18. The magnetic sensor device of claim 17, wherein the magnetic sensor array comprises a reference sensor.

19. The magnetic sensor system of claim 15, wherein the antiferromagnetic layer comprises a first ferromagnetic layer, a metallic layer, a second ferromagnetic layer, and an antiferromagnetic layer.

20. A method for evaluating whether an analyte is present in a sample, the method comprising:
contacting a magnetic sensor with a magnetically-labeled sample to generate a signal, the magnetic sensor comprising:
two or more magnetic tunnel junction (MTJ) magnetoresistive elements electrically connected to each other in series;
a first electrode contacting at least a portion of a surface of a first MTJ magnetoresistive element and extending beyond an edge of the surface of the first MTJ magnetoresistive element;
a second electrode comprising a first end contacting at least a portion of an opposing surface of the first MTJ magnetoresistive element and a second end extending beyond an edge of the opposing surface of the first MTJ magnetoresistive element and contacting at least a portion of a surface of a second MTJ magnetoresistive element, wherein at least one of the first and second electrodes contacts less than an entire surface of one or more of the first and second MTJ magnetoresistive elements; and an analyte-specific probe bound to a surface of the magnetic sensor, wherein:

facing surfaces of the first and second electrodes are only overlapping where they contact the surface and the opposing surface of the MTJ magnetoresistive elements, the first MTJ magnetoresistive element comprises a first free layer, the second MTJ magnetoresistive element comprises a second free layer, and the first and second MTJ magnetoresistive elements comprise a common antiferromagnetic layer and a common insulating layer between the antiferromagnetic layer and the first and second free layers, and the magnetic sensor is configured to detect a magnetically-labeled analyte in the sample;

obtaining a signal from the magnetic sensor; and evaluating whether the magnetically-labeled analyte is present in the sample based on the signal.

21. The method of claim 20, wherein the method comprises magnetically labeling the sample prior to the contacting.

22. The method of claim 21, wherein the evaluating comprises obtaining a signal from the magnetic sensor as the magnetically-labeled sample contacts the magnetic sensor.

23. The method of claim 22, wherein the signal is an analyte-specific signal.

24. The method of claim 20, wherein the contacting comprises applying a magnetic label to the magnetic sensor after contacting the magnetic sensor with the sample.

25. The method of claim 20, wherein the antiferromagnetic layer comprises a first ferromagnetic layer, a metallic layer, a second ferromagnetic layer, and an antiferromagnetic layer.

* * * * *